United States Patent
MacLean et al.

(10) Patent No.: US 8,067,012 B2
(45) Date of Patent: *Nov. 29, 2011

(54) TREATMENT OF MELANOMA USING HSV MUTANT

(75) Inventors: Alasdair Roderick MacLean, Glasgow (GB); Susanne Moira Brown, Glasgow (GB); Nigel William Fraser, Philadelphia, PA (US); Bruce Paul Randazzo, Philadelphia, PA (US)

(73) Assignees: Crusade Laboratories Limited, Glasgow (GB); The Wistar Institute, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/692,347

(22) Filed: Jan. 22, 2010

(65) Prior Publication Data

US 2010/0172872 A1    Jul. 8, 2010

Related U.S. Application Data

(63) Continuation of application No. 11/152,591, filed on Jun. 13, 2005, now Pat. No. 7,674,468, which is a continuation of application No. 08/776,350, filed as application No. PCT/GB95/01791 on Jul. 28, 1995, now abandoned.

(30) Foreign Application Priority Data

Jul. 29, 1994 (GB) .................................. 9415320.2

(51) Int. Cl.
*A61K 39/12* (2006.01)
*A61K 39/245* (2006.01)

(52) U.S. Cl. ................................. 424/205.1; 424/231.1

(58) Field of Classification Search ........................ None
See application file for complete search history.

(56) References Cited

U.S. PATENT DOCUMENTS

| | | | |
|---|---|---|---|
| 4,859,587 A | 8/1989 | Roizman | |
| 5,328,688 A | 7/1994 | Roizman | |
| 5,585,096 A * | 12/1996 | Martuza et al. .............. | 424/93.2 |
| 6,139,834 A * | 10/2000 | Martuza et al. .............. | 424/93.2 |
| 6,340,673 B1 | 1/2002 | Roizman et al. | |
| 2005/0226850 A1 | 10/2005 | Brown et al. | |

FOREIGN PATENT DOCUMENTS

| | | |
|---|---|---|
| EP | 0514603 | 5/2002 |
| WO | WO 92/04050 | 3/1992 |
| WO | WO 92/13943 | 8/1992 |
| WO | WO 93/19591 | 10/1993 |
| WO | WO 96/00007 | 1/1996 |
| WO | 96/03997 | 2/1996 |
| WO | WO 96/39841 | 12/1996 |
| WO | WO 97/12623 | 4/1997 |
| WO | 97/26904 | 7/1997 |
| WO | WO 97/26904 | 7/1997 |
| WO | 03/068809 | 8/2003 |
| WO | 2005/049844 | 6/2005 |
| WO | 2005/049845 | 6/2005 |
| WO | 2005/049846 | 6/2005 |
| WO | 2007/026146 | 3/2007 |
| WO | 2007/132169 | 11/2007 |
| WO | 2008/099189 | 8/2008 |
| WO | 2009/013448 | 1/2009 |

OTHER PUBLICATIONS

Chou et al (Science, 1990, 250:1262-1266, IDS).*
Davey et al (Neurosurgery, 1991, 28:8-14, IDS).*
Olofsson et al (Arch. Virol., 1993, 128:241-256, IDS).*
McKie et al (J of General Virology, 1994, 75:733-741, IDS).*
Chou et al. (1990) Science, 250:1262-1266, "Mapping of herpes simplex virus-1 neurovirulence to $\gamma_1 34.5$, a gene nonessential for growth in culture".
MacLean et al. (1991) Journal of General Virology, 72:631-639, "Herpes simplex virus type 1 deletion variants 1714 and 1716 pinpoint neurovirulence-related sequences in Glasgow strain $17^+$ between immediate early gene 1 and the 'a' sequence".
von Hoff et al. (1981) The American Journal of Medicine 70(5):1027-1041, "Association Between Human Tumor Colony-Forming Assay Results and Response of An Individual Patient's Tumor to Chemotherapy".
Kamb et al. (2007) Nature Reviews Drug Discovery 6(2):115-120, "Why is cancer drug discovery so difficult?" abstract only.
Amer, et al., "Malignant melanoma and central nervous system metastases," Cancer, vol. 42 (1978) pp. 660-668.
Andreansky, et al., "The Application of Genetically Engineered Herpes Simplex Viruses to the Treatment of Experimental Brain Tumors," PNAS, vol. 93 (1996) pp. 11313-11318.
Bindal, et al., "Sarcoma Metastatic to the Brain: Results of Surgical Treatment," Neurosurgery, vol. 35(2), (Aug. 1994), pp. 185-190.
Bolovan, et al., "ICP34.5 Mutants of herpes simplex virus type 1 strain 17syn+ are attenuated for neurovirulence in mice and for replication in confluent primary mouse embryo cell cultures," Journal of Virology, (Jan. 1994) pp. 48-55.
Boviatsis, et al., "Antitumor activity and reporter gene transfer into rat brain neoplasms inoculated with herpes simplex virus vectors defective in thymidine kinase or ribonucleotide reductase," Gene Therapy, vol. 1, (Sep. 1994) pp. 323-331.
Bowie, et al., "Deciphering the Message in Protein Sequences: Tolerance to Amino Acid Substitutions," Science, vol. 247, (1990) pp. 1306-1310.
Bronner-Fraser, et al., "The Neural Crest: What can it tell us about cell migration and determination," Current Topics in Developmental Biology, vol. 15, Chapter 1, (1980) pp. 1-25.
Budman, et al., "The current causes of death in patients with malignant melanoma," European J. Cancer, vol. 14, (1978) pp. 327-330.

(Continued)

*Primary Examiner* — Laura B Goddard
(74) *Attorney, Agent, or Firm* — Swanson & Bratschun, L.L.C.

(57) ABSTRACT

Use as an anti-cancer agent of a mutant herpes simplex virus wherein the mutant virus comprises a modification in the γ34.5 gene in the long repeat region ($R_L$) such that the γ34.5 gene is a non-functional, manufacture of medicaments and methods of testing cancer in mammals employing HSV mutant.

15 Claims, 9 Drawing Sheets

OTHER PUBLICATIONS

Figure 1A:
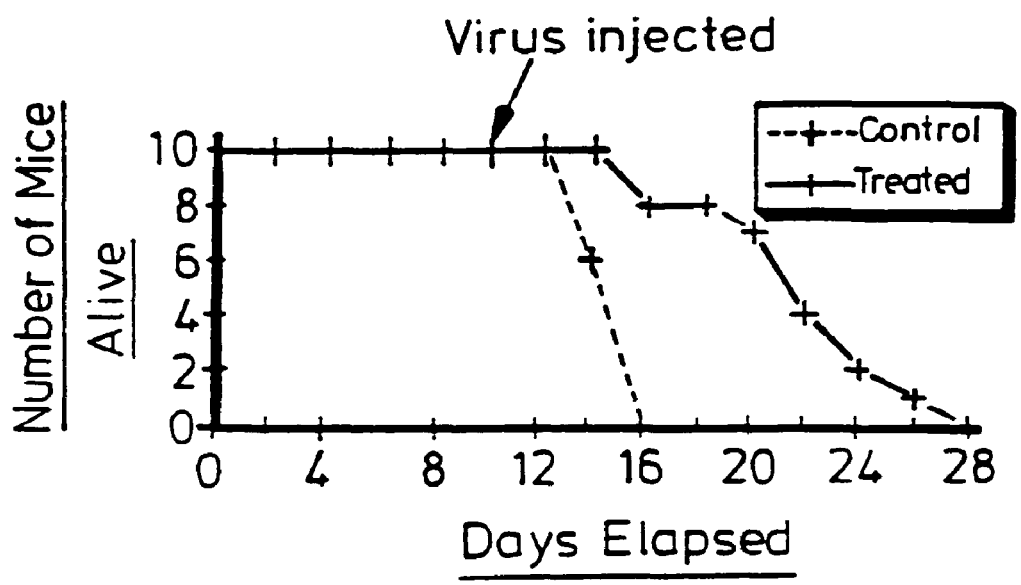

Carrel, et al., "Expression of Neuroectodermal Antigens Common to Melanomas, Gliomas and Neuroblastomas," Acta Neuropathol. (Berlin), vol. 57, (1982) pp. 158-164.

Cassel, et al., "Newcastle disease virus as an antineoplastic agent," Cancer, vol. 18, (1965) pp. 863-868.

Chou, J. et al., "Mapping of Herpes Simplex Virus-1 Neurovirulence to γ134.5, a Gene Nonessential for Growth in Culture," Science, vol. 250, (1990) pp. 1262-1266.

Coen, et al., "Thymidine kinase-negative herpes simplex virus mutants establish latency in mouse trigeminal ganglia but do not reactivate" PNAS, vol. 86, (1989) pp. 4736-4740.

Coukos, et al., "Oncolytic Herpes Simplex Virus-1 Lacking ICP34.5 Induces p53-independent Death and Is Efficacious against Chemotherapy-resistant Ovarian Cancer," Clinical Cancer Research, vol. 6 (Aug. 2000), pp. 3342-3353.

Dambach et al., "Oncolytic Viruses Derived from the γ34.5-Deleted Herpes Simplex Virus Recombinant R3616 Encode a Truncated UL3 Protein," Molecular Therapy, vol. 13(5), (May 2006) pp. 891-898.

Dang, et al., "Gene Therapy and Translational Cancer Research," Clinical Cancer Research, vol. 5 (1999) pp. 471-474.

Davey, et al., "Disposition of Cerebral Metastases from Malignant Melanoma: Implications for Radiosurgery," Neurosurgery, vol. 28, No. 1 (1991) pp. 8-15.

DeLuca, et al., "Isolation and Characterization of Deletion Mutants of Herpes Simplex Virus Type 1 in the Gene Encoding Immediate-Early Regulatory Protein ICP4," Journal of Virology, vol. 56(2), (Nov. 1985) pp. 558-570.

Deonarain, Mahendra "Ligand-Targeted Receptor-Mediated Vectors for Gene Delivery," Exp. Opin. Ther. Patents, vol. 8, (1998) pp. 53-69.

Dolan, et al., "Status of the ICP34.5 gene in herpes simplex virus type 1 strain 17," Journal of General Virology, vol. 73, (1992) pp. 971-973.

Goto, et al., "Oncolytic effect of newcastle disease virus on yoshida sarcoma ( I )," Jpn. J. Microbiol., vol. 3 (1959) pp. 171-181.

Hanada, et al., "Combined Effects of Acyclovir and Human Interferon-α on Herpes Simplex Virus Replication in Cultured Neural Cells," Journal of Medical Virology, vol. 29 (1989) pp. 7-12.

Harrington, et al., "A phase I/II dose escalation study of OncoVexGM-CSF and chemoradiotherapy in untreated stage III/IV squamous cell cancer of the head and neck," Institute of Cancer Research.

Hwu, et al., "Treatment of metastatic melanoma in the brain with temozolomide and thalidomide," The Lancet Oncology, retrieved online Jul. 3, 2009 at http://www.thelancet.com/journals/lanonc/article/PIIS1470-2045(01)00522-8/fulltext.

Javier, et al., "Genetic and Biological Analyses of a Herpes Simplex Virus Intertypic Recombinant Reduced Specifically for Neurovirulence," Journal of Virology, vol. 61(6), (Jun. 1987) pp. 1978-1984.

Kapplitt, M.G., et al., "Mutant Herpes Simplex Virus Induced Regression of Tumours Growing in Immunocompetent Rats," Journal of Neuro-Oncology, vol. 19, (1994) pp. 137-147.

Kesari, S., et al., "Therapy of Experimental Human Brain Tumours Using a Neuroattenuated Herpes Simplex Virus Mutant," Laboratory Investigation, vol. 73, No. 5, (1995) pp. 636-648.

Kucharczuk, et al., "Replication-restricted Herpes Simplex Virus-based Treatment of Localized Non-CNS Malignancy," Proc. Am. Assoc. Cancer Rest. 37:342 (1996).

Kucharczuk, et al., "Use of 'Replication-restricted' Herpes Virus to Treat Experimental Human malignant Mesothelioma," Cancer Res. 57:466-471 (1997).

Lallier, Thomas E., "Cell Lineage and Cell Migration in the Neural Crest," Cell Biology, Neuronal Migrations and Tuberous Sclerosis, Part 5, pp. 158-171.

Le Douarin, Nicole, "Migration and Differentiation of Neural Crest Cells," Current Topics in Developmental Biology, vol. 16, Chapter 2, (1980) pp. 31-85.

Liu, et al., "ICP34.5 deleted herpes simplex virus with enhanced oncolytic, immune stimulating, and anti-tumor properties," Gene Therapy (2003) pp. 292-303.

Mackie, et al., "Intralesional injection of herpes simplex virus 1716 in metastatic melanoma," The Lancet, vol. 357, (Feb. 17, 2001) pp. 525-526.

MacLean, et al., "Herpes simplex virus type 1 deletion variants 1714 and 1716 pinpoint neurovirulence-related Sequences in Glasgow Strain 17+ Between Immediate Early Gene 1 and the 'a' Sequence," J. Gen. Virol. 72:631-639 (1991).

Markert, J.M. et al., "Reduction and Elimination of Encephalitis in an Experimental Glioma Therapy Model with Attenuated Herpes Simplex Mutants that Retain Susceptibility to Acyclovir," Neurosurgery, vol. 32, (1993), pp. 597-603.

Martuza, et al., "Experimental therapy of human glioma by means of a genetically engineered virus mutant," Science, vol. 252, (1991) pp. 854-856.

Martuza, R.L., "Viral Vectors for Experimental Brain Tumour Therapy," Molecular Genetics of Nervous System Tumors, (1993) pp. 381-386.

McGeoch, et al., "The complete DNA sequence of the long unique region in the genomie of herpes simplex virus type 1," Virology, vol. 69, (1988) pp. 1531-1574.

McKie, et al., "Characterization of the herpes simplex virus type 1 strain 17+ neurovirulence gene RL1 and its expression in a bacterial system," Journal of General Virology, vol. 75 (1994), pp. 733-741.

McMenamin, et al., "Potential and Limitations of a γ34.5 Mutant of Herpes Simplex 1 as a Gene Therapy Vector in the CNS," Gene Therapy, vol. 5, (1998) pp. 594-604.

Miller, Cathie G., et al., "Development of a Syngenic Murine B16 Cell Line-Derived Melanoma Susceptible to Destruction by Neuroattenuated HSV-1," Molecular Therapy, Feb. 2001, vol. 3, pp. 160-168.

Mineta, et al, "Treatment of malignant gliomas using ganciclovir-hypersensitive, ribonucleotide reductase-deficient herpes simplex viral mutant," Cancer Research, vol. 54, (1994) pp. 3963-3966.

Mineta, et al., "Attenuated multi-mutated herpes simplex virus-1 for the treatment of malignant gliomas," Nature Medicine, vol. 1, (1995) pp. 938-943.

Montgomery, et al., "Herpes Simplex Virus-1 Entry into Cells mediated by a Novel Member of the TNF/NGF Receptor Family," Cell, vol. 87, (Nov. 1, 1996) pp. 427-436.

Olofsson, et al., "5-Propyl-2-deoxyuridine induced interference with glycosylation in herpes simplex virus infected cells," Archives of Virology (1993) 128:241-256.

Randazzo, et al., "Treatment of experimental intracranial murine melanoma with a neuroattenuated herpes simplex virus 1 mutant," Virology, vol. 211(1) (Aug. 1, 1995) pp. 94-101.

Randazzo, et al., "Herpes simplex 1716—an ICP 34.5 mutant—is severely replication restricted in human skin xenograft in vivo," Science Direct—Virology, vol. 223(2), (Sep. 1996) pp. 392-395.

Robertson, et al., "Peripheral replication and latency reactivation kinetics of the non-neurovirulent Herpes Simplex Virus Type 1 variant 1716," (Journal of General Virology, vol. 73 (1992) pp. 967-970.

Roizman, Bernard, "The Structure and Isomerization of Herpes Simplex Virus Genomes," Cell, vol. 16, (Mar. 1979) pp. 481-494.

Romano, et al., "Latest Developments in Gene Transfer Technology: Achievements, Perspectives, and Controversies over Therapeutic Applications," Stem Cells, vol. 18, (2000) pp. 19-39.

Sacks, W.R., and Schaffer, P.A., "Deletion Mutants in the Gene Encoding the Herpes Simplex Virus Type 1 Immediate-Early Protein ICP0 Exhibit Impaired Growth in Cell Culture," Journal of Virology, vol. 61(3), (Mar. 1987) pp. 829-839.

Scrip, "FDA Panel Rejects Temodal for melalnoma," No. 2423, Mar. 26, 1999, p. 16.

Senzer, et al., "Phase II Clinical Trial of a Granulocyte-Macrophage Colony-Stimulating Factor-Encoding, Second-Generation Oncolytic Herpesvirus in Patients with Unresectable Metastatic Melanoma," Journal of Clinical Oncology, downloaded from http://jco.ascopubs.org/cgi/doi/10.122/JCO.2009.24.3675 by Glasgow University Library on Nov. 4, 2009.

Senzer, et al., "Updated Results of a Phase II Clinical Trial with a Second Generation, Enhanced Potency, Immune-enhanced, Oncolytic Herpesvirus in Unresectable Metastatic Melanoma," Mary Crowley Cancer Research Centers.

Simpson, et al., "Combination of a Fusogenic Glycoprotein, Prodrug Activation, and Oncolytic Herpes Simplex Virus for Enhanced Local Tumor Control," Cancer Research, vol. 66(9) (May 1, 2006) pp. 4835-4842.

Spivack, et al., "Replication, establishment of latent infection, expression of the latency-asociated transcripts and explant reactivation of herpes simplex virus type 1 γ34.5 mutants in a mouse eye model," Journal of General Virology, vol. 76 (1995) pp. 321-332.

Suskind, et al., "Viral agents oncolytic for human tumors in heterologous host; oncolytic effect of Coxsackie B viruses,"Proc. Soc. Exp. Biol. Med., vol. 94, (1957) pp. 309-318.

Taha, et al., "A Variant of Herpes Simplex Virus Type 2 Strain HG52 with a 1.5 kb Deletion in $R_L$ between 0 to 0.02 and 0.81 to 0.83 Map Units is Non-neurovirulent for Mice," Journal of General Virology, vol. 70, (1989) pp. 705-716.

Tait, et al., "Ovarian Cancer BRCA1 Gene Therapy: Phase I and II Trial Differences in Immune Response and Vector Stability," Clin. Cancer Research, vol. 5 (1999) 1708-1714.

Thompson, et al., "Herpes Simplex Virus Neurovirulence and Productive Infection of Neural Cells is Associated with a Function Which Maps between 0.82 and 0.832 Map Units on the HSV Genome," Virology, vol. 172, (1989) pp. 435-450.

Toda, et al., "Treatment of Human Breast Cancer in a Brain Metastatic Model by G207, a Replication-Competent Multimutated Herpes Simplex Virus 1," Human Gene Therapy, vol. 9 (Oct. 10, 1998) pp. 2177-2185.

Verma, et al., "Gene Therapy—Promises, Problems and Prospects," Nature, vol. 389 (1997) pp. 239-242.

Vieweg, et al., "Considerations for the Use of Cytokine-Secreting Tumor Cell Preparations for Cancer Treatment," Cancer Investigation, vol. 13 (1995) pp. 193-201.

World Health Organization Classification of Tumours, Pathology & Genetics, Tumours of the Nervous System, "Glioblastoma—definition," Edited by Paul Kleihues & Webster K. V. Cavenee, International agency for Research on Cancer (IARC) Press Lyon, 2000, 33 pages.

Zimmermann, H.M., "Malignant Lymphoma of the Nervous System," Acta Neuropathol. Suppl. VI (Berlin), vol. 6 (1975), pp. 69-74.

Zudaire et al, "Adrenomedullin and cancer," Regulatory Peptides, vol. 112, (2003) pp. 175-183.

* cited by examiner

TREATMENT OF MELANOMA USING HSV MUTANT

CROSS-REFERENCE TO RELATED APPLICATIONS

This application is a continuation of U.S. patent application Ser. No. 11/152,591, filed Jun. 13, 2005, now U.S. Pat. No. 7,674,468, filed Jun. 13, 2005, which is a continuation of U.S. patent application Ser. No. 08/776,350, filed Apr. 18, 1997, which is the U.S. National Stage of International Application No. PCT/GB95/01791 filed Jul. 28, 1995 (published in English under PCT Article 21(2)), which in turn claims the benefit of Great Britain Application No. 9415320.2, filed Jul. 29, 1994. These applications are incorporated herein in their entirety.

Incorporated by reference herein in its entirety is the Sequence Listing, entitled "Sequence project ST25.txt," which was created Mar. 11, 2010, size 1 kilobyte.

FIELD OF INVENTION

The present invention relates to the use of a herpes simplex virus (HSV) mutant for the treatment of cancer tumors, particularly those of the brain or nervous system whether the tumors are metastatic tumors or primary tumors.

BACKGROUND

The DNA sequence of herpes simplex type 1 (HSV-1) is known (references 13,25) and is linear with a length of about 152k residues. It consists of two covalently linked segments, designated long (L) and short (S). Each segment contains a unique sequence flanked by a pair of inverted terminal repeat sequences. The long repeat ($R_L$) and short repeat ($R_S$) are distinct. The unique long ($U_L$) region includes genes UL1 to UL56, and the $U_s$ region includes genes US1 to US12.

A relatively large number of patients with advanced cancers will develop metastatic lesions in the brain and spinal cord. This frequently results in severe and debilitating neurological complications including headache, paralysis, seizures, and impaired cognition. It has been estimated that 70,000 cancer deaths occur each year in the United States with metastatic lesions to the central nervous system (CNS). Radiation and steroids are presently the principle therapies used, however, they are only palliative, and frequently cause significant neuropsychological and endocrinological morbidity. Surgery is generally reserved for removal of solitary metastases, and is often not curative (1).

Viral therapy for the destruction of tumors is not a new concept. Effects in various experimental tumor systems have been demonstrated using parvovirus H-1, Newcastle disease virus, retroviral vectors containing drug susceptibility genes, and Herpes Simplex Type I virus (HSV-1) (2-7). The mechanisms by which viruses improve the outcome in experimental tumor systems are complex and poorly understood. Brain tumors represent a dividing cell population occurring within an essentially non-dividing cell population of support cells, and terminally differentiated neurons. Thus, in the context of brain tumor therapy, one rationale is to select a virus that replicates exclusively or preferentially in dividing cells. Such a virus may be capable of establishing a lytic infection exclusively in tumor cells within the CNS, ultimately destroying the tumors without infecting surrounding brain, and without deleterious effects to the host.

Pioneering experiments with HSV showed a dose dependent improvement in survival of nude mice bearing intracranial human gliomas following intratumoral therapy with mutant HSV-1 dlspTK (3). This virus has a deletion in the viral thymidine kinase (TK) gene, (8) and exhibits a relatively neuro-attenuated phenotype in mice (9). However, dlspTK infection of tumor bearing animals causes histologically evident encephalitis (3). The use of TK' mutantsof HSV-1 for viral therapy also has an inherent major disadvantage in that these viruses are resistant to the clinically effective anti-viral agents acyclovir and ganciclovir (10).

The terminal 1 kb of the long repeat region ($R_L$) of the HSV-1 and HSV-2 genomes contain a gene (11-13), that confers neurovirulence. Deletion or mutation of this gene ($\gamma34.5$), results in variants that grow as well as wild type virus on dividing cells of many established cell lines, but show impaired replication on non-dividing cells (12-14). In mice, $\gamma34.5$ null mutants are incapable of replicating in the central nervous system, and do not cause encephalitis (12,15-16).

A mutant HSV-1 called R3616, containing a 1000 base pair (bp) deletion in $\gamma34.5$, with an $LD_{50}$ (minimum dose of virus that kills 50% of infected animals) that is at least $3 \times 10^3$ fold greater than wild type F strain virus from which it was derived (12), has been shown to improve the outcome of nude mice bearing intracranial human gliomas (17). In the work presented here, we have utilized an HSV-1 strain 17 mutant virus called 1716, that has a 759 by deletion in $\gamma34.5$ (16).

The construction of mutant virus 1716 is described in published patent application WO92/13943 (PCT/GB92/00179) the contents of which are incorporated herein by reference. However, this patent publication is solely concerned with the use of mutant 1716 as a vaccine, either in itself or as a vector vaccine which includes a heterologous gene coding for an antigen.

Melanoma is a prevalent malignancy. Cerebral metastases occur in up to 75% of patients with metastatic disease, and are among the most common causes of death (18-22). Presently, the life span of patients with CNS melanoma is short, ranging from 2 to 7 months (23).

It is an object of the present invention to provide an improved HSV-based viral therapy of cancer tumors.

STATEMENT OF INVENTION

The present invention in one aspect provides the use as an anticancer agent of a mutant herpes simplex virus which has been modified in the $\gamma34.5$ gene of the long repeat region ($R_L$) such that the gene is non-functional.

The invention also relates to a method of treatment of cancer in a mammal (human or animal) by the administration to the mammal of an anti-cancer effective dose of the mutant herpes simplex virus.

DETAILED DESCRIPTION

For the purposes of the present invention "non-functional" means that the gene has been modified by deletion, insertion or substitution (or other change in the DNA sequence such as by rearrangement) such that it does not express the normal product or a functionally equivalent product. The effect of the non-functionality of the gene is that the neurovirulence of the virus to the patient is substantially removed.

Thus the invention is based on the finding that rendering the $\gamma34.5$ gene non-functional provides an HSV mutant which is particularly effective in destroying dividing tumor cells, whilst at the same time the HSV mutant does not replicate within normal non-cancerous cells. It therefore has the potential to provide a safe anti-cancer treatment.

Two types of herpes simplex virus are known HSV-1 and HSV-2 and either may be employed in the present invention to provide the HSV mutant. Inter-type recombinants containing DNA from both types could also be used.

The modification may be effected at any convenient point within the γ34.5 gene, and such point generally corresponds to a restriction enzyme site. The modification may be within the Bam H1 s restriction fragment of the $R_L$ terminal repeat (corresponding to 0-0.02 and 0.81-0.83 mu). The modification is typically a deletion of 0.1 to 3 kb, particularly 0.7 to 2.5 kb. In this work a 759 deletion in γ34.5 was made in the HSV-1 mutant, referred to as 1716. HSV strain 1716 has been deposited at the Health Protection Agency, Porton Down, and European Collection of Cell Cultures at Porton Down, Salisbury Wiltshire SP4 0J9, UK on 28th Jan. 1992 and given the deposit reference 92012803. This deposit was made under the Budapest Treaty on the International Recognition of the Deposit of Microorganisms, and all restrictions imposed by the depositor on the availability to the public of the deposited material will be irrevocably removed upon the grant of the patent.

The HSV genome also includes a number of other genes which are non-essential to the successful culturing of the virus. It is, of course, necessary to retain within the HSV mutant the ability to culture the mutant so that the mutant is self-replicating and stocks of the mutant can be grown in tissue culture. Lethal modifications of the genome which remove the ability to culture the HSV mutant are not acceptable.

However, in addition to the primary modification to the γ34.5 gene of the $R_L$ region, it may be advantageous to also include in the HSV mutant one or more secondary non-lethal modifications within non-essential genes.

The present invention also encompasses as a new product an HSV mutant which includes in addition to the primary modification, a secondary non-lethal modification (for example within Vmw65). The mutant may be derived from HSV-1 or HSV-2.

In a similar way, other secondary modifications may involve modification of the latency associated transcript (LAT) promoter so as to render the promoter non-functional and prevent transcription thereof.

Herpes simplex virus infects the brain and nervous system. The HSV mutant is effective against primary tumors originating within the brain and nervous system, but is particularly useful against metastatic tumors where cancer cells originating elsewhere have lodged in the brain or nervous system (particularly the central nervous system (CNS)). Brain metastases occur commonly in a variety of human cancers (e.g. melanomas), and at present such cases are invariably fatal. The efficacy of treatment according to the invention employing the HSV mutant will depend on the time after origination of the tumor at which the treatment is initiated, but efficacy is improved by early treatment for example in 1 to 30 days.

The $LD_{50}$ (minimum dose of virus that kills 50% of infected animals) of the 1716 mutant in respect of mice is $10^6$ fold greater than that of the wild type 17+ virus from which it is derived. Thus the neurovirulence of 1716 is essentially removed relative to the wild type virus.

The effective non-toxic dose of HSV mutant can be determined by routine investigation by the skilled addressee, and will depend on a number of factors including the particular species of mammal and the extent of development of the tumor. A guide can be obtained from the Examples herein.

In a further aspect of the invention there is provided a method of treating cancer in mammals, in particular in humans by administering a pharmaceutical formulation comprising the HSV mutant to mammals, in particular to humans. Thus, the method of treatment can comprise the administration of a pharmaceutical formulation comprising the HSV mutant by injection directly into the tumour or parenterally into the blood stream feeding the tumour.

It will usually be presented as a pharmaceutical formulation including a carrier or excipient, for example an injectable carrier such as saline or apyrogenic water. The formulation may be prepared by conventional means.

Embodiments of the invention will now be described by way of example only.

Figure 1B:
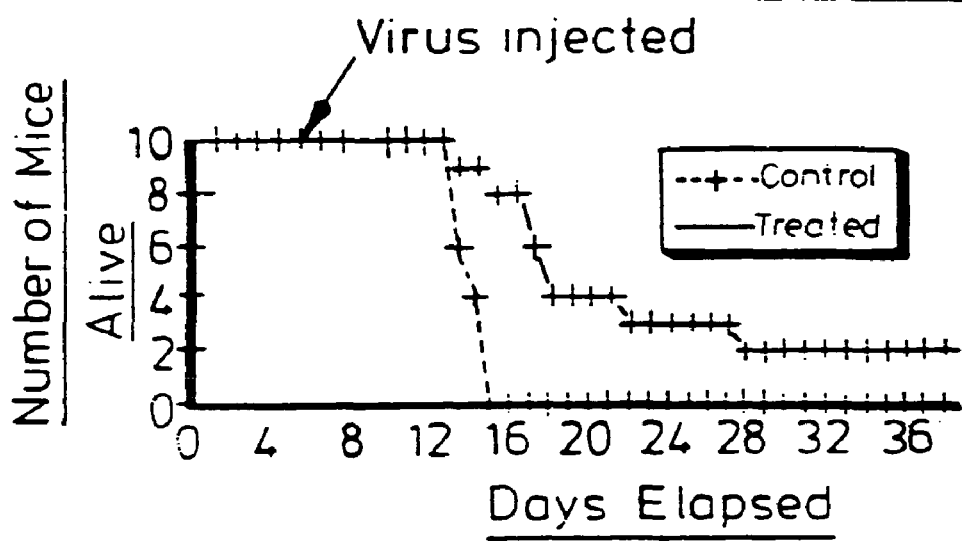
Figure 2:
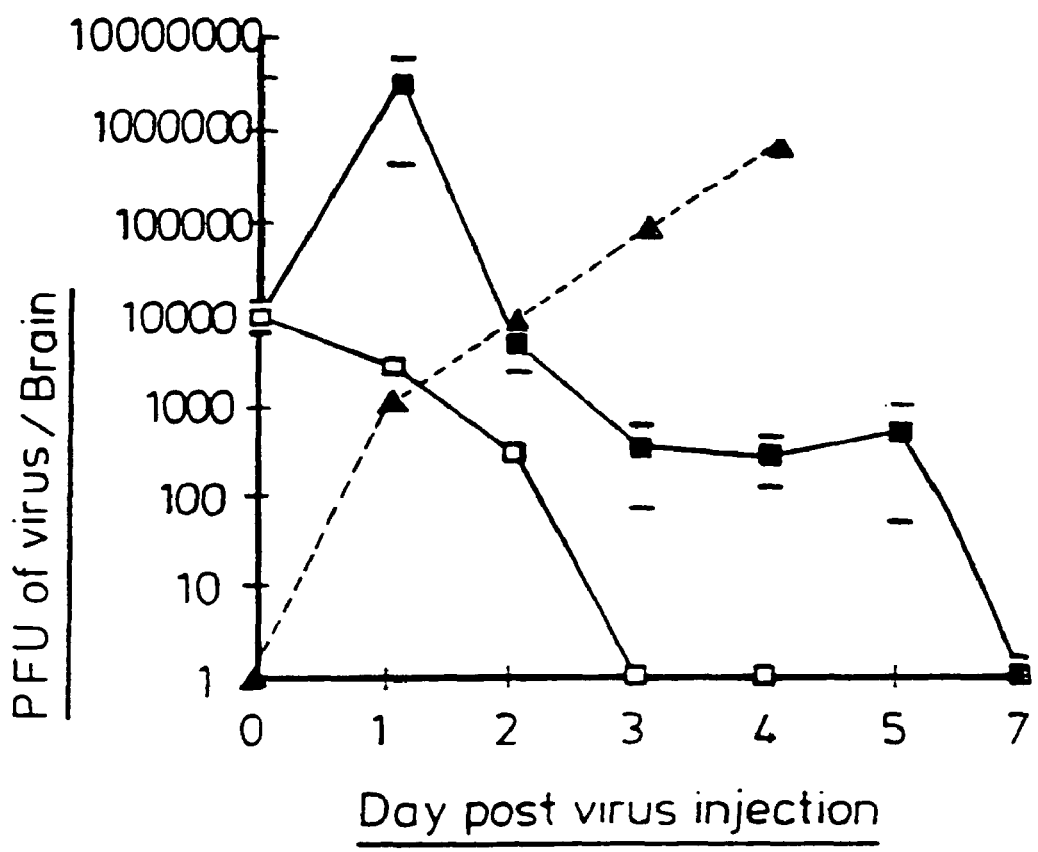

FIGS. 1 and 2 show the results of experiments described fully in Examples 3 and 5 respectively.

FIG. 1: Survival Curves

Tumor-bearing mice injected at 10 days (FIG. 1b) and at 5 days (FIG. 1b) post tumor injection with HSV-1 mutant 1716.

FIG. 2: Relative replication rates of HSV-1 mutant

Relative replication rates of HSV-1 mutant 1716 in brain tumor (closed squares); and of 1716 and wild type 17+ in non-tumor brain (open squares and closed triangles respectively).

Figure 3:
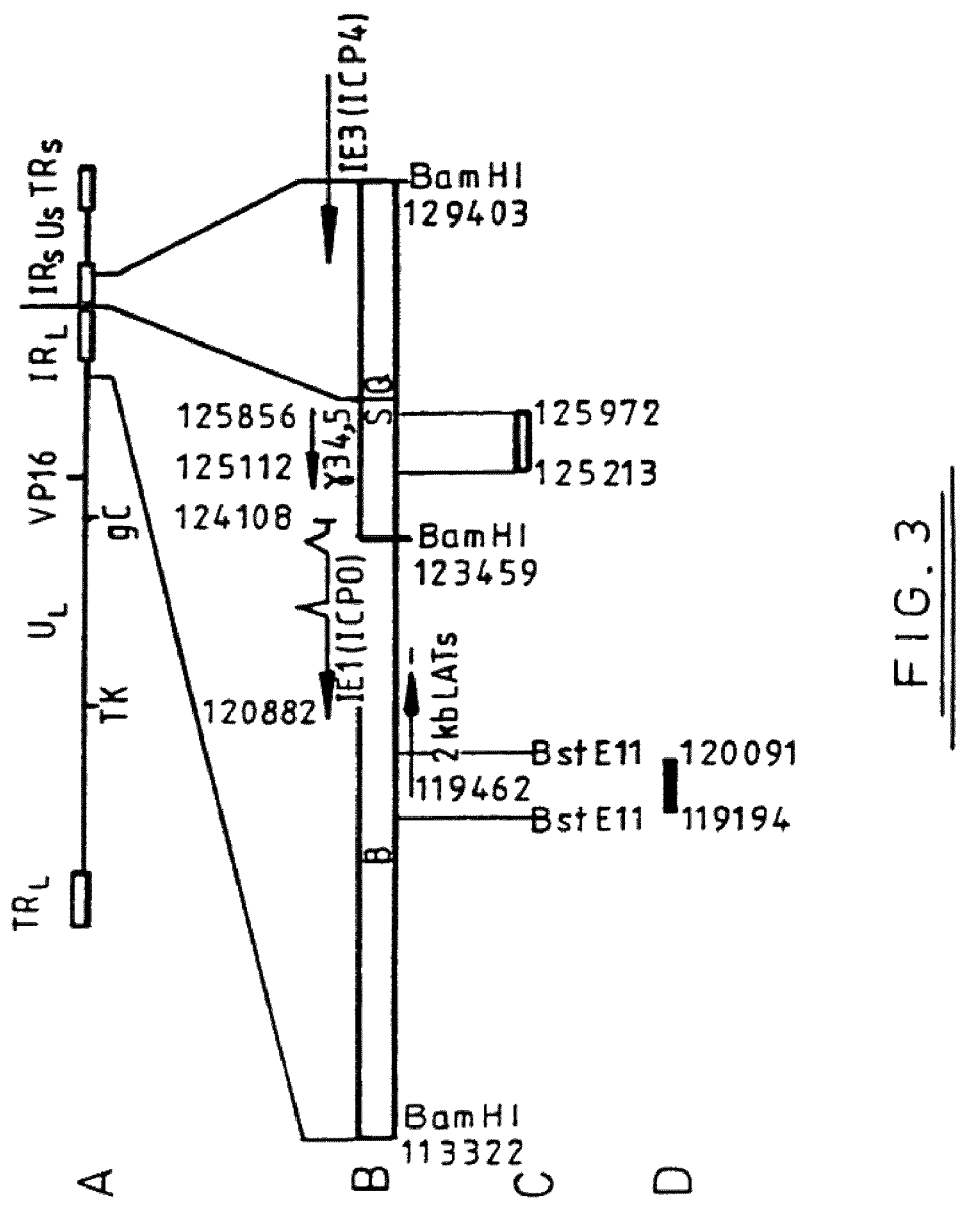

FIG. 3: RSV-1 Genome map.

HSV-1 genome showing approximate location of the γ34.5, 2 kb latency associated transcript (LAT) and neighbouring genes. A. The 152 kb HSV-1 strain 17+ genome, illustrating the unique long and short segments of the genome, $U_L$ and $U_S$ (lines), bounded by internal (IR) and terminal repeat (TR) regions (open boxes). Hatch marks show location of the VP16, thymidine kinase (TK) and glycoprotein C (gC) genes. B. Expanded view of the $U_L/U_S$ region of the genome the location of the γ34.5, ICPO and ICP4 mRNAs and the location of the 2.0 kb LAT which is expressed during acute and latent infection. C. The location of the 759 by deletion in strain 1716. D. The location of the LAT specific BstEII-BstEII probe used for in situ detection of HSV specific gene expression. Nucleotide positions are based on DNA sequence analysis of Perry and McGeoch (45).

Figure 4:
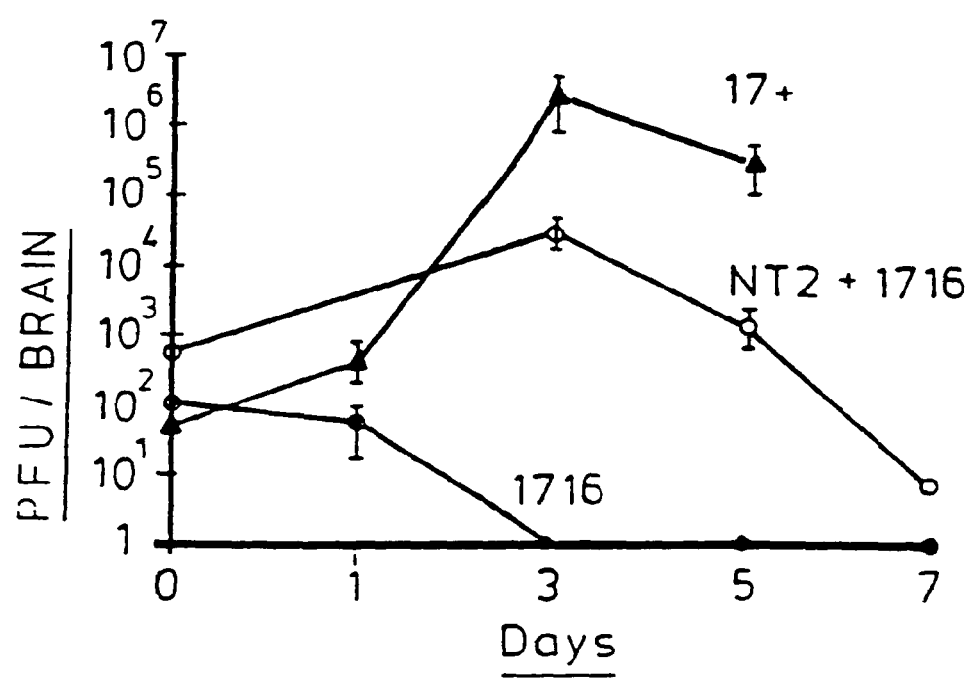

FIG. 4: Quantification of infectious virus in nude mouse brain after IC inoculation.

To investigate the extent of strain 1716 replication in brain tumors, nude mice were injected with NT2 cells. Twelve days later each mouse was infected with $5 \times 10^5$ PFU of strain 1716 at the same stereotactic coordinates (open circles). At the times indicated, mice were sacrificed, the brains were frozen in Liquid $N_2$ and stored at $-70°$ C. Specimens were thawed rapidly, homogenized, and viral titration was performed in triplicate on BHK cells. To establish the growth characteristic of strain 1716 and parental 17+ in brain without tumor, mice were injected intracranially with either $5 \times 10^4$ PFU of 1716 (closed circles) or $1 \times 10^6$ PFU of 17+ (closed triangles). Mice were sacrificed at the times shown and processed as described in Methods. Each point is the mean of 2 mice with SEM bars.

Figure 5:
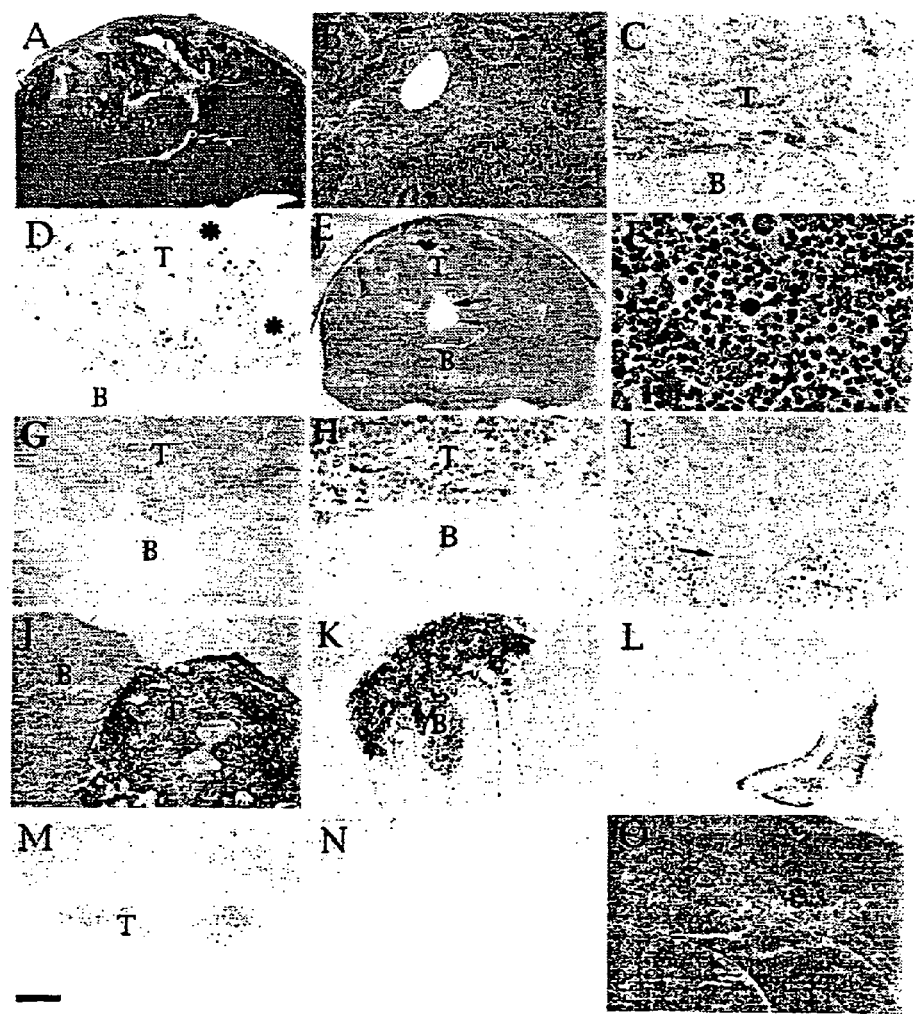

FIG. 5: Detection of replicating virus by immunohistochemistry and in situ hybridization Nude mice were IC injected with $3 \times 10^4$ NT2 cells. 14 days later they were inoculated with $5 \times 10^5$ PFU of 1716. A. Control mice with tumor after 14 days. B. Tumor is histologically very diverse, arrows: tubular structures. C. MOC-1 antibody specifically identifies the NT2 tumor cells. D. Antibody MIB-1 identifies cycling cells. Note low number of labeled cells in tubular structures (asterisk). E. 14 day tumor after three days infection with strain 1716. The arrow indicates a region of extensive tumor lysis and necrosis. F. Infected cells show characteristic features of herpes infected cells such as intranuclear inclusion bodies formation, cytomegaly and necrosis. G. Herpes antigen is limited to tumor cells. H. Virus replicates in tumor cells at interface between tumor and host brain shown using anti-HSV antibodies. I. The kinetics of viral replication are delayed at 3 days after infection in the tubular structures compared to surrounding non-tubular cells as shown with anti-HSV antibodies. The arrow identifies a rare HSV antigen positive tubular cell. These tubular structures are lysed at later days after infection. J. Herpes gene expression is also limited to tumor by in situ hybridization (black grains). K and L. Wild-type virus (17$^+$) replicates in brain and tumor and spreads throughout the whole brain. M. H&E of 14 day tumor 18 days after infection with strain 1716. Note the small size of tumor. N. Viral antigen and O. viral gene expression is strikingly limited to the residual tumor mass. Abbreviations: T=tumor; B=host brain (Scale Bar:=1.2 mm in A; =62.5 µm in B,C,D; =2.0 mm in E&G; =12 µm in F; =450 µm in H, M, N, O; =90 µm in I; =200 µm in J; =900 µm in K and L).

Figure 6:
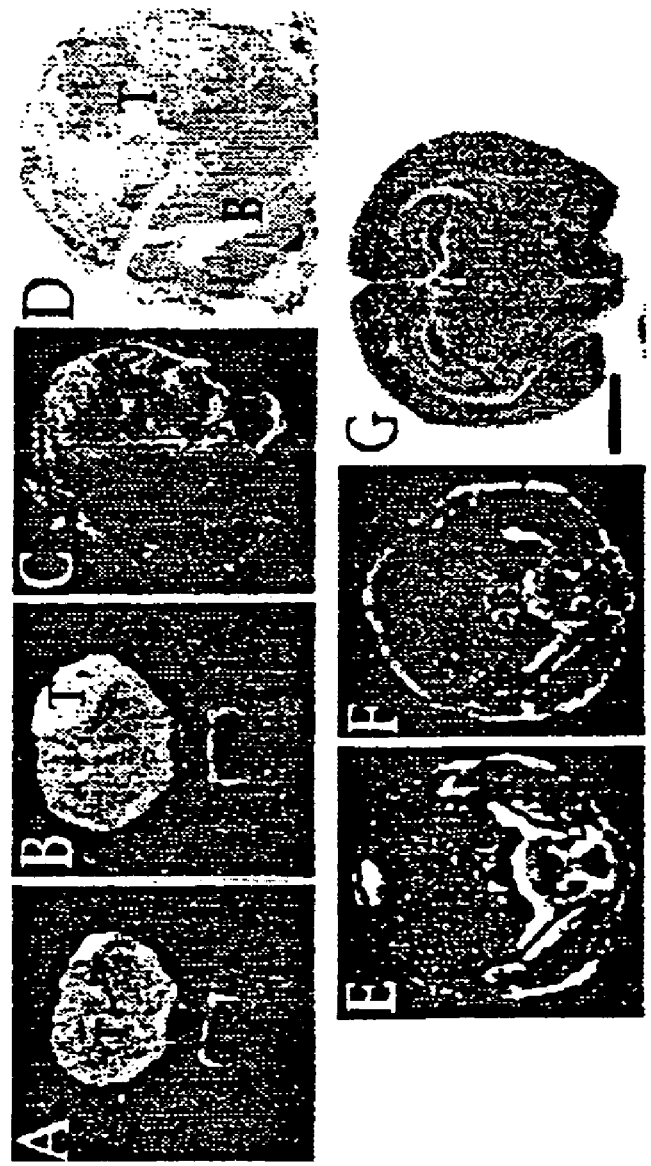

FIG. 6: MRI analysis of treated and untreated NT2 tumors.

Nude mice were injected stereotactically with $3 \times 10^4$ NT2 cells and 11 days later (d11 post-tumor cell implantation) T1 weighted, gadolinium-enhanced MRIs (A,E) were performed. The presence of a tumor (T) is confirmed by the white enhancing lesion appearing in the superior right hemisphere in these mice. These sections show the area of the maximal tumor mass in cross section. The following day these mice were inoculated with either $5 \times 10^5$ PFU of strain 1716 or culture medium. In control mice, the tumor progressed over time and IC volume increased dramatically (B: day 32 post-tumor: C & D: day 41 post-tumor). In strain 1716 treated mice the tumor regressed and showed no evidence of live tumor cells or virus in the brain (F & G: day 36 post-tumor), (Scale Bar: =2.77 mm in D & G).

Figure 7:
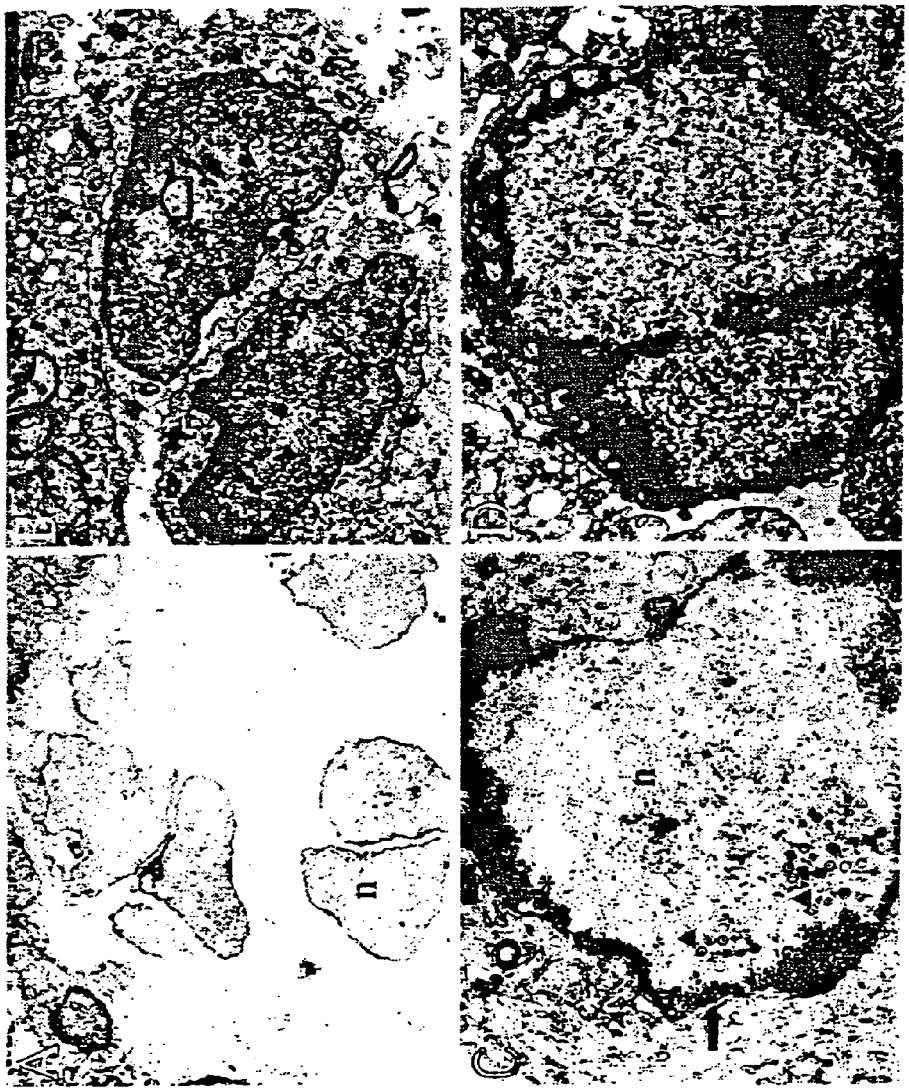

FIG. 7: Electronmicroscopy

Tumors from nuce mice which were mock inoculated or inoculated with strain 1716 were harvested and processed for electronmicroscopy. A: Electronmicrograph of uninfected tumor cells. B: EM of NT2 tumor cells early in infection DNA condensation and viral domains (open arrow) can be observed; C: NT2 tumor cells late in infection, marginated chromatin (*) and viral particles (arrowhead) can be observed, D: A dividing cell that is infected, arrow: nuclear membrane, c: cytoplasm, n: nucleus (original magnifications at 2500×).

Figure 8:
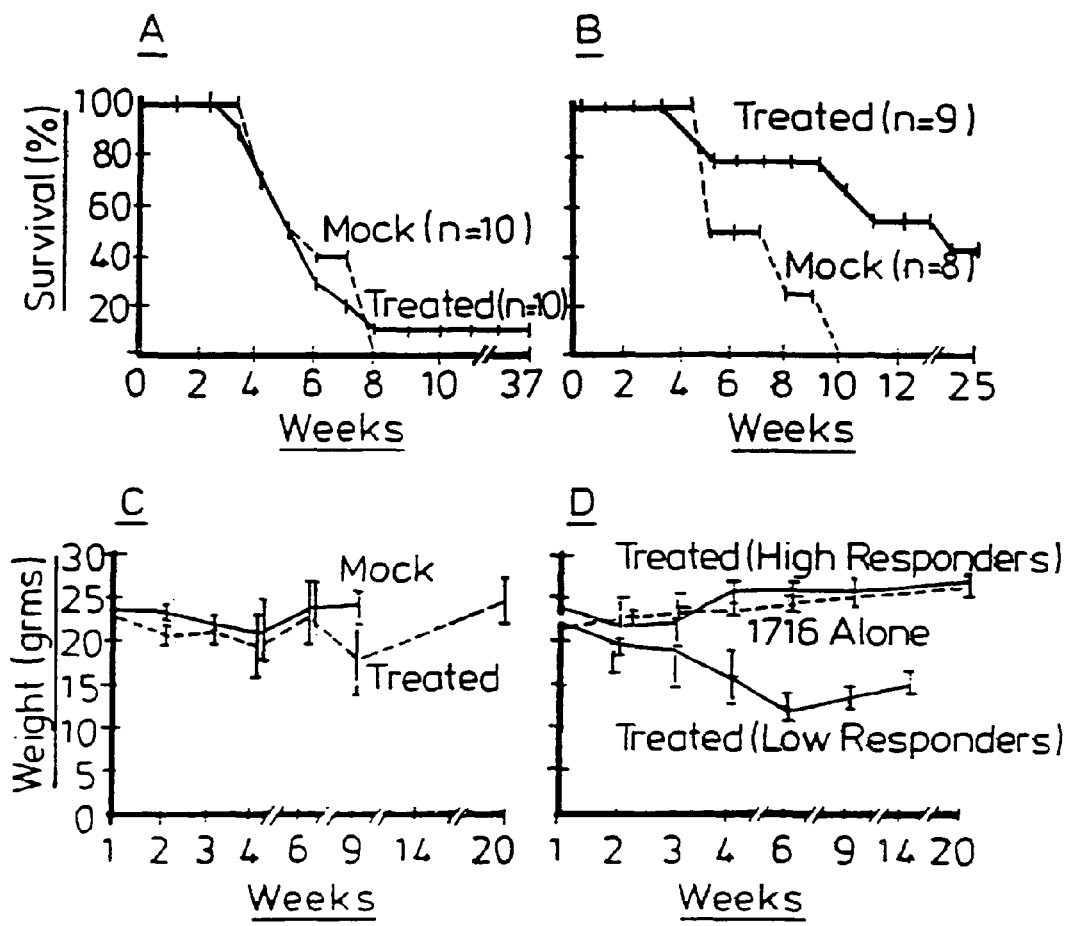

FIG. 8: Prolonged survival of NT2 tumor bearing mice treated with strain 1716.

A: Survival Experiment (Table 1, Study V)-20 nude mice were stereotactically injected with $3 \times 10^4$ NT2 cells. Twelve days later, 10 mice were sterotactically injected with $5 \times 10^5$ PFU/5 µl of strain 1716 (treated, closed circle) and 10 mice were mock injected with 5 µl of viral culture medium (mock, closed triangle). B: Survival Experiment (Table 1, Study VI)- 17 nude mice were stereotactically injected with $3 \times 10^4$ NT2 cells. Ten days later, 9 mice were stereotactically injected $5 \times 10^5$ PFU/5 µl of strain 1716 (treated, closed circle) and 8 mice were mock injected with 5 µl of viral culture medium (mock, closed triangle). C: Weight Graph—Weights of control (closed triangle) and treated mice (closed circles) from Study VI (Table 1; FIG. 6B). D: Weights of treated group separated into long-term survivors (HR, closed circle) and dead (LR, closed square) compared with strain 1716 alone treated mice (Study 1, Table 1; closed triangle). Standard Error of the Mean (SEM) bars are included.

Figure 9:
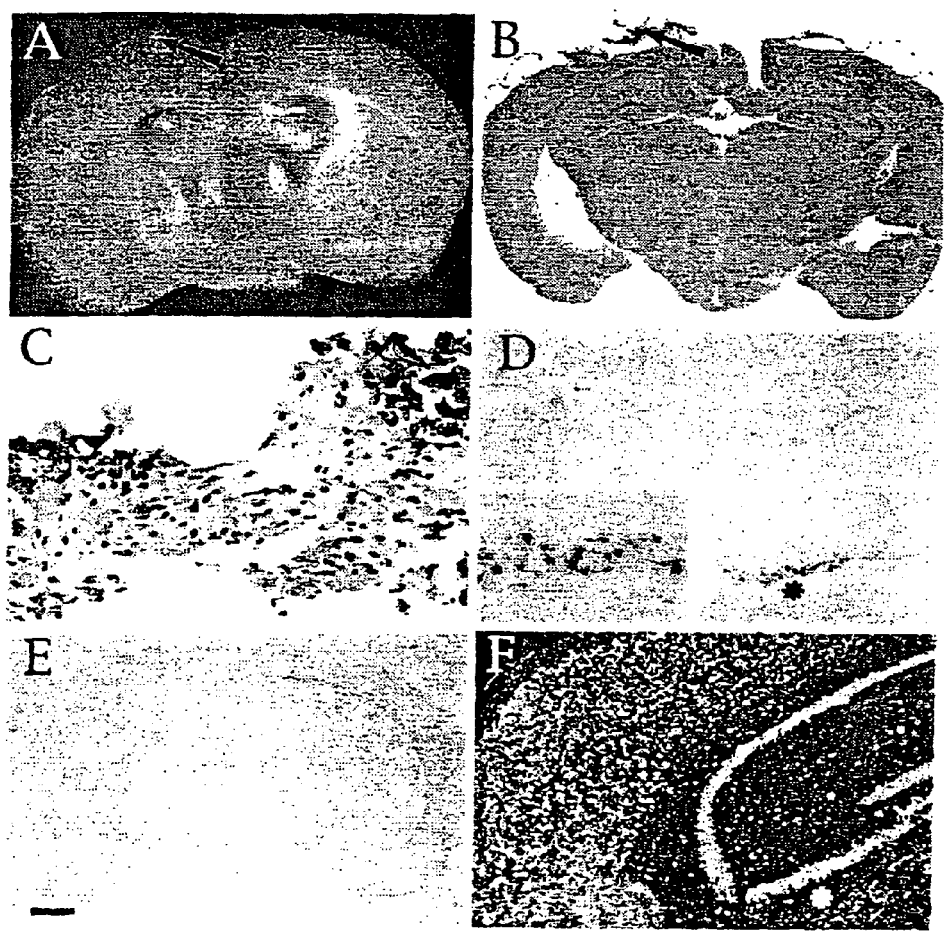

FIG. 9: Detection of virus in long-term survivors by immunohistochemistry and in situ hybridization.

Long-term survivors were sacrificed and brains and other organs were fixed, sectioned and used for immunohistochemical detection of NT2 cells and HSV and in situ detection of HSV. A: The arrow identifies residual scar at tumor implantation site. B: On histology the brain shows no evidence of any tumor cells (arrow) or replicating virus. C: The residual scar site consists of dystrophic calcifications. This is a higher power view of region identified by the arrow in B. D: Latent virus was observed in the hippocompus (asterisk) of these survivors (4 months post-infection) and the insert shows the nuclear localised signal of LAT positive cells. E: MBP staining shows no evidence of demyelination in the whole brains of these mice. F: Dark-field photomicrograph of in situ hybridization performed using a radiolabeled poly(dT) probe to detect total poly (A) $^+$RNA in cells as a measure of metabolic health of the LAT positive cells (asterisk). The experimental tissue (A serial section from 7D) was compared to uninfected, mock infected and RNAse treated tissue. There was no detectable difference in the signal in LAT positive area in adjacent serial section. (Scale Bar: =1.2 mm in A, B, E; =113 µm in D and −90 µm in insert; =113 µm in F; =45 µm in C).

EXAMPLES

Section 1

Materials and Methods
Animals:
Female C57B1/6 mice (4 to 6 weeks old—weight approximately 20 g) were obtained from The Jackson Laboratory (Bar Harbor, Me.).
Tumor Cells:
S91 Cloudman melanoma cells were obtained from the ATCC (Rockville, Md.). B16, and Harding-Passey melanoma cells were a generous gift from Dorothee Herlyn (Wistar Institute, Phila, Pa.). Cells were grown in plastic flasks in AUTO-POW media containing penicillin, streptomycin, and 5% calf serum. When originally obtained, all cell lines were grown up, and then frozen in 95% calf serum/5% DMSO, so that all experiments could be initiated with cells of a similar passage number. On the day of intracranial injection, cells in sub-confluent monolayer culture were passaged with 0.25% trypsin solution in EDTA, washed x1 in cell culture media, resuspended at the appropriate concentration in media without serum, and held on ice.
Intracranial Tumor Production:
Mice were anaesthetized with I.M. ketamine/xylazine (87 mg/kg ketamine/13 mg/kg xylazine). The head was cleansed with 70% EtOH. A small midline incision was made in the skin of the head exposing the skull. Stereotactic injection of tumor cell suspension was performed using a small animal stereotactic apparatus (Kopf Instruments, Tujunga, Calif.). Injections were done with a Hamilton syringe through a disposable 28 g. needle. The needle was positioned at a point 2 mm caudal of the bregma and 1 mm left of midline. Using a separate 27 g. needle with a shield that limits the length of the needle exposed to 0.5 mm, the skull was breached at the appropriate coordinates. The injection needle was advanced through the hole in the skull to a depth of 2 mm from the skull surface and then backed-out 0.5 mm to create a potential space. $1 \times 10^5$ cells in a total volume of 2 µL were injected over 1 minute. Following the injection, the needle was left in place for 3 minutes, and then slowly withdrawn. The skin was sutured closed.
Virus:
To produce virus stocks, subconfluent monolayers of baby hamster kidney 21 clone 13 (BHK) cells were infected with HSV strains in 1814, 1716, dlspTK, or wild type 17+. Virus was concentrated from the culture and titrated by plaque assay as previously described (28). All viral stocks were stored frozen in viral culture medium (AUTO-POW media containing penicillin, and streptomycin) at −70° C., and thawed rapidly just prior to use.

Viral Inoculation:

Mice anesthetized with I.M. were ketamine/xylazine, and the head was cleansed with 70% EtOH. Using a Hamilton syringe with a 30 gauge disposable needle, the appropriate amount of virus was injected ($10^4$-$10^6$ PFU in 2 µL) through a midline incision at the same stereotactic coordinates used for tumor cell injection. The injection was performed over 1 minute, and following the injection the needle was left in place for 3 minutes, and then slowly withdrawn.

Magnetic Resonance Imaging:

Mice were imaged using a 1.9 Tesla 30 cm bore animal MRI system located in the Hospital of the University of Pennsylvania MRI facility. Animals were anesthetized with I.M. ketamine/xylazine (87 mg/kg ketamine/13 mg/kg xylazine). Subsequently, each animal was injected with 10 units of Gd (DTPA) via a tail vein. The animal was taped in place within a plexiglass gradient coil and imaged.

Immunohistochemistry:

HSV-infected cells were detected by an indirect avidin-biotin immunoperoxidase method (Vectastain ABC Kit, Vector Labs, Burlingam, Calif.) as specified by the manufacturer with slight modification. Briefly, tissue sections were deparaffinized, rehydrated, quenched in peroxide ($H_2O_2$) and blocked in 3.5% goat serum (Sigma Chem. Co., St. Louis, Mo.). Tissue sections were incubated overnight at 4° C. with the primary antibody, a rabbit antiserum to HSV-1 (Dako Corp., Carpinteria, Calif.), used at a dilution of 1:1000. Next, the tissue was incubated at room temperature with biotinylated goat anti-rabbit IgG, the avidin-biotin horseradish peroxidase complex and finally AEC substrate. Sections were counter stained with hematoxylin and examined under the light microscope. As a control for the specificity of immunostaining, tissues were processed as above, except that non-immune rabbit serum was substituted for the primary HSV-1 antiserum.

Titration of Virus from Tumor and Brain:

Mice were sacrificed by lethal injection of anesthesia. Brains with or without in situ tumors were removed aseptically, snap frozen in liquid nitrogen, and stored at −70° C. Each tissue sample was rapidly thawed in a 37° C. water bath, and the tissue was homogenized in viral culture medium at a 10% weight/volume ratio using a Pyrex Ten Broeck tissue grinder. The homogenates were centrifuged at 3,000×g for 10 minutes at 4° C. The supernatant of each tissue homogenate was diluted logarithmically in media, and the viral titer of each was determined by plaque assay on BHK cells (28).

Statistics:

Standard deviation, and t-Test: two sample assuming unequal variances, were calculated using Microsoft Excel (Redmond, Wash.) on an apple Macintosh computer (Cupertino, Calif.).

Example 1

Lysis of Melanoma Cells

In our initial studies, we wanted to make a straightforward in vitro determination of the relative abilities of HSV-1 wild type and mutant viruses to lyse various murine melanoma cells. We also wanted to compare how efficiently these melanoma cells were lysed by HSV-1 relative to baby hamster kidney (BHK) cells, which is a standard cell line used to propagate and titer HSV-1. Cells were plated in 24 well tissue culture plates at a density of $5\times10^4$ cells/well. The viruses were diluted logarithmically and cell monolayers were infected in triplicate. After 72 hours of culture, the highest dilution of virus at which complete destruction of the monolayer still occurred, was recorded for each virus-cell combination. Data are expressed as the number of PFU of virus, obtained for each virus-cell combination.

As demonstrated in Table 1, the various mutant viruses lyse melanoma cells and BHK with efficiencies similar to wild type 17+. Cloudman S-91, and H-P melanoma cells were lysed efficiently relative to BHK.

Example 2

Tumor Production

The capacity of each melanoma cell line to produce intracranial tumors was then evaluated. For each cell line, 10 C57B1/6 mice were injected stereotactically with $5\times10^4$ cells in the right cerebral hemisphere. Mice were observed daily, and sacrificed when they appeared moribund, or after 6 weeks if they remained asymptomatic. Each brain was fixed, sectioned, stained, and examined histologically for tumor. Both H-P and B-16 formed intracranial tumors in 10 of 10 C57B1/6 mice, while Cloudman S-91 only formed a tumor in 1 of 10 mice.

We decided to proceed with the H-P model, since these cells were both susceptible to lysis by the relevant HSV-1 mutants, and formed brain tumors efficiently.

Subsequent experiments verified that stereotactic injection of H-P cells into the brain of C57B1/6 mice establishes tumors in 100% of the animals. A technical advantage of this system is that the presence of a brain tumor can be verified by magnetic resonance imaging (MRI) prior to treatment, or simply by observation of a pigmented area on the skull overlying the tumor site, generally by 5 days post cell injection. The tumors progressed to a size that caused the mice to become moribund from neurologic symptoms in approximately two weeks.

Example 3

Treatment of Brain Tumors with HSV-1 Mutant 1716

C57B1/6 mice were injected stereotactically in the right cerebral hemisphere with $5\times10^4$ Harding-Passey melanoma cells. After 10 days (FIG. 1a) or 5 days (FIG. 1b), $5\times10^3$ PFU of HSV 1716 was injected at the same stereotactic coordinates. The number of days elapsed between injection of tumor cells and time mice became moribund is shown on the X axis. Control mice were injected with an equal volume of viral culture medium at the appropriate time.

As shown in FIG. 1a stereotactic injection of HSV-1 mutant 1716 into brain tumors 10 days after establishment, resulted in a statistically significant increase in the length of time elapsed until the mice become moribund (P(T<=t) one-tail: $1.016\times10^{-4}$). However, no long term survivors were obtained. When viral therapy was performed 5 days after tumor establishment (FIG. 1b), significant improvement in outcome was again seen in the treatment group (P(T<=t) one-tail: $7.707\times10^{-3}$), and 2/10 treated mice were cured. One long term survivor was sacrificed after day 39 post viral infection. Microscopic examination of serial sections of the brain did not reveal any residual tumor (data not shown). The second animal is still alive and asymptomatic at greater than 150 days post treatment. Treated animals that became moribund, showed progression of their brain tumors upon examination of tissue sections.

Example 4

1716 Replication in Tumor and Non-Tumor Cells

Immunohistochemistry shows that replication of 1716 is in fact restricted to tumor cells, and does not occur in surrounding brain. A significant number of melanoma cells within tumor were stained by polyclonal antiserum to HSV-1 on days 3 and 6 post infection. Moreover, in tumor bearing mice treated with 1716, no HSV-1 antigen staining was seen in brain tissue adjacent to tumor or in any other areas of brain in all sections examined. In addition, no histologic evidence of encephalitis was seen in any 1716 treated mice at any time. In contrast, tumor bearing mice infected with wild type 17+ virus, exhibited multiple focal areas of HSV-1 immunohistochemical staining both within tumor and in surrounding and distant brain as well. A significant encephalitis characterised by polymorphonuclear leukocytes, nuclear dust, and extravasation of red blood cells, is seen in areas of this and other sections examined. In control experiments, no immunohistochemical staining was seen with anti-HSV-1 in tumor or brain from mice who did not receive virus, or in virally infected brain tumor sections subjected to the full immunohistochemical protocol with normal rabbit serum substituted for the primary anti-HSV-1 antibody (data not shown).

Example 5

Kinetics of Replication in Tumor and Non-Tumor Cells

Having shown striking restriction of 1716 replication to tumor by immunohistochemistry, we next attempted to quantify the kinetics and extent of replication of 1716 in tumor by titration of infectious virus, and compare this with titration data from non-tumor bearing mouse brain infected with 1716 or 17+.

To investigate the extent of 1716 replication in brain tumors, C57Bl/6 mice were injected with Harding Passey melanoma cells right of midline. Seven days later each mouse was infected with $5 \times 10^5$ PFU of 1716 at the same stereotactic coordinates. At the times indicated, mice were sacrificed, the brains were frozen in liquid $N_2$ and stored at $-70°$ C. Specimens were thawed rapidly, homogenized, and viral titration was performed in triplicate on BHK cells (closed squares). These data represent the mean of 4 mice at each time point.

To establish the growth characteristic of 1716 and wild type 17+ in brain without tumor, mice were injected intracranially with either $5 \times 10^5$ PFU 1716 (open squares) or $1 \times 10^3$ PFU of 17+(closed triangles). Mice were sacrificed at the times shown and processed as described above. Each point is the mean of 2 mice.

As shown in FIG. 2, wild type 17+ virus replicated efficiently in non-tumor bearing mouse brain. In contrast, no replication of 1716 occurred in brain of non-tumor bearing mice. The titer of virus recovered decayed over time, and infectious 1716 could only be isolated for 3 days after inoculation. However, when 1716 was injected into brain tumors, significant replication occurred as evidenced by recovery of an amount of infectious 1716 on day 1 post inoculation that is substantially greater than the input amount. Under these conditions, infectious 1716 could be isolated from tumor bearing mice for 5 days post inoculation, but not on day 7. These results clearly demonstrate that HSV-1 mutant 1716 will freely replicate in tumor cells (leading to their destruction) but does not replicate in non-tumor cells (leaving them unharmed).

TABLE 1

Relative susceptibility of melanoma cells to lysis by HSV-1.

| | Cell Type | | |
|---|---|---|---|
| Virus | Cloudman S91 | Harding-Passey | BHK |
| dlspTK | $10^3$ | $10^4$ | $>10^3$ |
| 1716 | $10^4$ | $10^4$ | $-10^3$ |
| 17+ (wild type) | $10^3$ | $10^3$ | $>10^2$ |

EXAMPLES

Section 2

Materials & Methods

Virus Stocks

To produce virus stocks, subconfluent monolayers of baby hamster kidney 21 clone 13 (BHK) cells were infected with HSV strains 1716, in1814, or parental 17+. Strain in1814 has a mutation (insertion) in the VP16 gene (located in the $U_L$ region; FIG. 3A) and strain 1716 has a mutation (deletion) in the γ34.5 gene (mutant; FIG. 3C). Virus was concentrated from the culture, titered on BHK cells by plaque assay and stored at $-70°$ C. in 0.5 ml aliquots of viral culture medium (AUTO-POW media containing penicillin and streptomycin) and thawed rapidly just prior to use as described (30,34).

Culture of Tumor Cells and Differentiation of NT2

NTera-2 (clone D1) cells (referred to here as NT2 cells) were cultured as described (28,29). Briefly, the cells were passaged 1:3 twice per week in OptiMEM with 5% fetal bovine serum (FBS) and penicillin/streptomycin (P/S). The medulloblastoma cell lines, D283 MED and DAOY, were cultured in RPMI 1640 with 10% FBS, 1% P/S and 1% Glutamine. BHK cells were cultured in AUTO-POW with 5% FBS, 1% P/S and 1% Glutamine. NT2 cells were plated at a density of $2.0 \times 10^6$ in T75 flask, and fed twice weekly with DMEM-HG supplemented with 10% FBS, 1% P/S, and $10^{-5}$M retinoic acid for 5 weeks. The differentiated NT2N cells were separated from non-neuronal cells as described (29,35). On the day of intracranial injection, NT2 cells in sub-confluent monolayer culture were harvested, washed three times in buffer and placed on a bed of ice until injected into the brains of nude mice.

Plaque Assay

NT2, BHK, DAOY and D283 MED cells were plated in 24 well tissue culture plates at a density of $10^5$ cells/well. The ciruses of interest were diluted logarithmically and cell monolayers were infected in triplicate with multiplicity of infections (MOI) ranging from 10 to 0.01. Cultures were observed regularly for the degree of cytopathic effects (CPE) of the viruses and noted for each MOI.

Titration of Virus from Cell Cultures

Cells were infected at MOI=1, harvested at 4, 24 and 48 hrs post-infection and stored at $-70°$ C. The samples were freeze-thawed twice from $-70°$ C. to $37°$ C., centrifuged at $3,000 \times g$ for 10 minutes at $40°$ C., the supernatant was diluted logarithmically in media and the viral titer of each sample was determined by plaque assay on BHK cells (34).

Titration of Virus from Tumor and Brain

To titrate viral inoculums in tumor and brain, nude mice were intracranially inoculated with $1 \times 10^6$ PFU of strain 17+ or $6.25 \times 10^4$ PFU of strain 1716 and the mice were sacrificed by lethal injection of anesthesia (ketamine/xylazine). The brains and tumors were dissected from mice that were sacrificed on different days post viral inoculation (day 0, 1, 3, 5 and 7), quick frozen in liquid nitrogen and stored at −70° C. The brain and tumor samples from the different time points were rapidly thawed in a 37° C. water bath, and the tissue was homogenized in viral culture medium at a 10% weight/volume ratio using a Pyrex Ten Broeck tissue grinder. The homogenates were centrifuged at 3,000×g for 10 minutes at 4° C., the supernatant was diluted logarithmically in media and the viral titer of each sample was determined by plaque assay on BHK cells (34).

Intracerebral Graft Implantation

Female homozygous nude mice (4 to 6 weeks old) were obtained from Harlan Sprague Dawley (Indianapolis, Ind.), the mice were anesthetized with intramuscular (IM) ketamine/xylazine (87 mg/kg ketamine/13 mg/kg xylazine) and stereotactic injections of tumor cell suspensions were performed using a small animal stereotactic apparatus (Kopf instruments, Tujunga, Calif.), a 10 µl Hamilton syringe and a 30 gauge disposable needle as previously described (35). To make cortical tumors, the syringe needle was positioned at a point 2 mm rostral of the bregma and 1 mm to the right of midline. The skull was cleansed with 70% ethanol and perforated with a 27 gauge needle and the Hamilton syringe with the attached needle was advanced through the hole in the skull to a depth of 1.5 mm below the dura and $3 \times 10^4$ NT2 cells in a total volume of 2 µl were injected over 5 min. Prior to implantation, NT2N cells were suspended in DMEM/HG and maintained at 40° C. in an ice bath. Exactly 5 µl of the NT2N cell suspension, containing approximately $5 \times 10^3$ cells, was injected at the same location as above. Following the injection, the needle was left in place for 5 min and then slowly withdrawn over 2 min. and the superficial skin wound was closed with sutures. The mice were allowed to recover and inspected daily for signs of illness. Body weight and cranial measurements with calipers were taken weekly. Any mice that showed signs of morbidity in extremis were sacrificed and brains were prepared for histochemistry. Tissues from some animals that died unobserved in their cage also were harvested and fixed for histochemical analysis. The experiments on nude mice are summarised in Table 2.

Viral Inoculation

Control mice and mice previously inoculated with tumor cells were anesthetized as described above and the head was cleansed with 70% ethanol. Using a Hamilton syringe with a 30 gauge disposable needle, the appropriate amount of virus was injected ($10^4$-$10^6$ PFU in 5 µl) through a midline incision at the same stereotactic coordinates used for the previous injection of tumor cells. The injection was performed over 3 min following the injection and then slowly withdrawn over 1 min. Control mice received equivalent volume inoculations of viral medium.

Magnetic Resonance Imaging

The brains of selected mice were imaged using a 30 cm bore 1.9 Tesla animal Magnetic Resonance Imaging (MR1) system (General Electric). To accomplish this, mice were anesthetized as described above at various times after implantation of tumor cells and inoculation of the tumor sites with virus. Subsequently, each animal was injected with 10 units of an enhancing agent, gadolinium complexed to a DTPA carrier (Magnevist), via a tail vein. The animal was then immobilised within a Plexiglas RF coil and imaged.

Immunohistochemical Procedures

Mice were transcardially perfused and fixed with 70% ethanol in isotonic saline (150 nM NaCl, pH 7.4) or 4% paraformaldehyde (0.1M PBS. pH 7.4) and the brain as well as samples of multiple other tissues (i.e. trigeminal ganglions, heart, proximal jejunum, liver, spleen, left kidney, femur, and vertebral bodies) were dissected for histological and immunohistochemical analysis. The methods for tissue processing and light microscopic immunohistochemical analysis were similar to those described elsewhere (35,36). Both monoclonal and polyclonal antibodies to neuronal and glial cytoskeletal proteins and other polypeptides that have been shown to serve as molecular signatures of the neuronal or glial phenotype were used for the immunohistochemical characterisation of intracranial allografts (35,37). Rabbit polyclonal antisera to HSV-1 which detects the major glycoproteins present in the viral envelope and at least one core protein (Dako Corp., Carpinteria, Calif.) was used at a dilution of 1:1000 to detect replicating virus (38). A mouse monoclonal antibody (MOC-1) to neural cell adhesion molecule (NCAMs) specific for human NCAMs was used at a dilution of 1:100 to detect NT2 and NT2N cells and to distinguish them from mouse brain cells (35). Another monoclonal antibody, RMO93 (1:10), which recognises rodent specific epitopes of the middle molecular weight neurofilament (NF-M) protein and does not cross-react with human NF-M was used to confirm the identity of NT2N grafts (35). RMO301 (1:100) is a monoclonal antibody that recognises human specific NF-M was used to confirm NT2N grafts. M13, a mouse monoclonal antibody which recognises human microtubule associated protein-2 (MAP2), was used at a 1:500 dilution. Rabbit polyclonal antibody specific to mouse myelin basic protein (MBP) was used at a dilution of 1:1000 (gift of A. McMorris). Tissue sections for staining with M1B-1 (a mouse monoclonal antibody that recognises a cell-cycle specific antigen (Ki-67) used at a 1:20 dilution; AMAC, Westbrook, Me.) were pretreated by microwaving on 10 mM Sodium Citrate as described (39). Prior to sacrifice some control mice were injected with intraperitoneally with bromodeoxyuridine (BrdU) at 5 mg/g (in 150 mM NaCl, 7 mM NaOH) body weight in order to label NT2 cells undergoing cell division in the grafts as described (37). Segments of the proximal intestine were removed from the same mouse as positive controls for cycling cells. BrdU positive cells were identified by using an BrdU antibody BU-33 (1:250). Antigen expressing cells were detected by the indirect avidin-biotin immunoperoxidase (Vectastain ABC kit, Vector Labs, Burlingam, Calif.) or peroxidase anti-peroxidase detection systems with 3,3'-diaminobenzadine (DAB) as the chromagen. Grafts and spread of virus in all animals was monitored by screening every tenth section through entire brain with MOC-1, MIB-1 and HSV antibodies.

In Situ Hybridization for HSV-1 Specific Gene Expression.

Sections of perfused and fixed tissue were mounted on slides and in situ hybridization was performed as previously described to detect viral gene expression (26,33,40). Serial tissue sections were hybridized with a $^{35}$S-labeled HSV LAT specific probe (BstEII-BstEII, FIG. 1E), with a $^{35}$S-labeled HSV specific thymidine kinase probe (tk; an early gene product) or with a biotinylated HSV specific gC (a late gene product) probe.

Preparation of $^{35}$S-Labeled Nick-Translated Probe

The latency-associated transcript (LAT) probe BstEII-BstEII subfragment (0.9 kb) of BamHI B was isolated from restriction digests by gel electrophoresis and purified by GeneClean (Bio 101 Inc.; La Jolla, Calif.; see FIG. 3) (30). The 3.4 kb BamHI fragment encoding the tk gene was isolated as described (41). DNA probes were nick-translated and separated from unicorporated nucleotides by passage through Sephadex G-50 spin columns (Pharamacia) (33). The specific activities of the probes were approximately $1-5 \times 10^8$ c.p.m/µg DNA.

Preparation of $^{35}$S-Labeled Poly (dT) Probe

A 21-mer of poly(dT) was synthesized and was used as substrate for labeling by terminal deoxynucleotidyl transferase (TdT). Reaction mix consisted of 2 µl of TdT, 1 µl of Poly(dT) (6 µg/µl), 5 µl of 5×TdT Buffer, 6 µl of CoCl$_2$ (2.5 mM), 10 µl of $^{35}$S-dTTP (1 µg), 1 µl of ddH$_2$O. The mix was incubated at 37° C. for 30 min. and was separated from unincorporated nucleotides by passage through Sephadex G-25 spin columns. In situ hybridization was performed exactly as above except that hybridization and washes were performed at 37° in 25% formamide (42). Exposure time courses were performed on uninfected, mock infected, wild-type virus infected and RNase treated tissue sections and were used as positive and negative controls for experimental tissue sections (see 43).

Biotinylated qC Probe to Detect Active Viral Replication.

A nonisotopic in situ hybridization was performed using a 21 by antisense gC probe (nucleic acids 199-219 of gC transcript, CGGGGCGGGGGTGGCCGGGGG; gift by K. Montone; FIG. 3F) linked to the 3' end by a biotinylated tail [5'-(TAG)$_2$-BBB-3']. The protocol was essentially the same as in Wang and Montone with slight modifications for mouse brain tissue.

DNA Nick End Labeling By TUNEL Method

The terminal deoxynucleotidyl transferase (TdT) dUTP-biotin nick end labeling (TUNEL) technique was performed as previously described (37). Briefly, deparaffinized and rehydrated slides were digested with 20 µg/ml of proteinase K in 0.1 M Tris (pH=8) at room temperature for 15 min. After washing, the sections were incubated with a mixture containing 20 mM biotinylated-dUTP, 0.3 U/µl terminal deoxynucleotidyl transferase, 1.5 mM cobalt chloride, 200 mM sodium cacodylate, 25 mM Tris, 0.25 mg/ml bovine serum albumin (pH=6.6) at 37° C. for 45 min. The reactions were stopped by washing in 2×SSC for 15 min. and the results were visualized by alkaline phosphatase conjugated with streptavidin and developed with Fast Red substrate. Coronal sections of postnatal day eight rat brain were used as positive controls for this TUNEL protocol because this was the developmental stage at which peak apoptosis activity was recognised (44).

Electron Microscopy of Thin Sections.

Portions of tumor tissues from perfused mouse brains were fixed in 1% glutaraldehyde, 4% paraformaldehyde in 0.1M sodium cacodylate (pH=7.4) over night at 4° C. and washed in sodium cacodylate buffer and processed for EM as described (37).

Statistics

Survival and weight statistics were performed using BMDP Statistics Software (ed. WJ Dixon; Release 7.0; 1993). Differences in survival in control and treated groups were compared using Generalised Wilcoxon (Breslow) Analysis. Differences in weights were compared using the t-test and the Mann-Whitney Test. Moribund animals in extremis were sacrificed and treated the same as animals found dead in their cage for statistical analysis.

Example 6

HSV-1 Strain 1716 Lyses and Spreads on Monolayers of Tumor Derived Human Neural Cell Lines In Vitro To determine how efficiently HSV-1 strain 1716 lyses rapidly dividing NT2 in comparison with parental strain 17$^+$, NT2 cells were plated on 24 well plates 1 day prior to infection by these two strains at Multiplicities of Infection (MOI) of 10, 1 and to 0.1. Both viruses, at MOI of 10, lysed NT2 cells within 1 day and this was associated with the characteristic morphological changes (rounding up, phase brightness, cytomegaly, plaque formation and loss of adhesion) associated with HSV infection. Since the behaviour of a virus at a low MOI (0.1) in vitro may predict the ability of a virus to spread in a tumor in vivo, we studied infection at MOI-0.1. Strain 1716 spread and destroyed monolayers of NT2 cells less efficiently than 17$^+$ (1716 lysed monolayer in 3 days and 17$^+$ in 2 days). The behaviour of these viruses was similar in two different human medulloblastoma cell lines (D283 MED and DAOY) suggesting that strain 1716 can lyse many different brain tumor cell lines.

Next, NT2N cells (the neuron-like retinoic acid differentiated derivatives of NT2 cells) were infected with these viruses. Strain 1716 was attenuated for cytopathicity in these cells with respect to strain 17+ and Lactate Dehydrogenase (LDH) assays for cytotoxicity performed on NT2N cells infected with the above viruses showed that both viruses caused some non-specific toxicity within 12 hours after infection (data not shown). Interestingly, titration of virus from infected cell cultures showed that strain 1716 was deficient for replication in NT2N cells (data not shown). Because strain 1716 is more severely neuroattenuated in mice than the other engineered strains (26, 30), we conducted in vivo studies of strain 1716 versus 17$^+$ virus inoculated into the CNS of nude mice with and without transplants of in vitro derived NT2N cells or with tumors established from transplanted NT2 cells. Reference is made to Table 2.

Example 7

Replication of HSV-1 Strain 1716 Cannot be Detected in the Mouse CNS Following Intracerebral Inoculation Consistent with previous results using SCID mice (26), intracerebral (IC) inoculation of 5×10$^6$ plaque forming units (PFU) of strain 1716 in nude mice did not induce clinical symptoms for over 4 months post-inoculation, and there was no evidence of encephalitis on histological analysis of the brains nor any evidence of replication in the major organs (e.g. liver, spleen, bone marrow, etc.) of these mice (Table 2, Study I). In contrast to strain 1716, IC inoculation of less than 100 PFU of strain 17$^+$ killed nude mice within 5-10 days and histopathological analysis revealed extensive cytopathic lesions (e.g. intranuclear inclusion bodies, cell death, etc.) in these mice (not shown).

To monitor viral replication in the brain after IC inoculation of strain 1716 versus strain 17$^+$, a viral titration assay was performed (Table 2, Study II). The Recovery of both viruses on day 0 was low relative to the amount of virus in the injected inoculum. This probably was due to adsorption or fusion of the viral particles to the membranes in the brain homogenates and to inactivation of virus during harvesting. FIG. 4 shows that the titer of strain 17$^+$ exponentially increased with time and resulted in morbidity and death of inoculated mice. In contrast, the titer of strain 1716 dropped precipitously in the brains of nude mice, and virus was no longer detectable 3 days post-inoculation. Moreover, there was no immunohistochemical evidence of encephalitis in strain 1716 infected mice, and there was no detectable spread of strain 1716 virus outside the CNS as evidenced by the absence of virus in samples of liver, spleen, kidney, jejunum and bone marrow by immunohistochemistry and by in situ hybridization for HSV specific transcripts (data not shown). Likewise, direct inoculation of liver or intravenous injection with strain 1716 did not cause any morbidity or death in nude mice. In contrast to strain 1716, strain 17+ infected mice exhibited evidence of encephalitis and tumor lysis (see FIG. 4).

Example 8

HSV-1 Strain 1716 Lytically Replicates In NT2 Tumors but not in Transplanted NT2N Cells in the Mouse CNS When strain 1716 was injected into NT2 tumors significant replication occurred for 7 days as evidenced by increase in viral titer over input inoculum by day 3 (FIG. 4). This is in agreement with the immunohistochemical and in situ hybridization data which showed no detectable strain 1716 in the brains of these mice except in the NT2 tumor cells for as long as they were present to support viral replication (see below).

Since quantification by titration assay in mice showed that strain 1716 replicated in NT2 cell tumors, we tested the ability of strain 1716 to induce regression of these tumors (Table 2, Study IV). To do this we injected 5 μl of strain 1716 containing $5 \times 10^5$ PFU into tumors that formed in the brains of nude mice following IC implantation of $3 \times 10^6$ NT2 cells. To monitor the fate of transplanted NT2 cells, mice were sacrificed at different time points after the viral inoculation and their brains and organs were anlysed by immunohistochemistry and in situ hybridization. NT2 cells formed tumors with a neural and epithelial histology in 100% of mice, and these tumors were lethal within 5 weeks after grafting (FIGS. 5A, 5B). These tumors contained abundant proliferating cells as evidenced by BrdU labeling, the immunohistochemical detection of cell cycle antigens and their rapid growth (FIGS. 5C, 5D). FIGS. 5E,F,G and H show that infection of NT2 tumors with strain 1716 is not uniform at day 3 post-infection (pi). This may reflect the localised nature of the injection site, or to cell-type specific differences in the vulnerability of the cells to infection and lysis by strain 1716. Nonetheless, most tumor cell types near the injection site harbored immunoreactive virus by day 5. At later days post-infection, more cells were infected, but immunoreactivity for virus in the tumor was weaker presumably due to clearance of the virus following lysis of the infected tumor cells (FIG. 5).

As seen in FIG. 5H, viral antigen is limited to the tumors. On high magnification, the infected tumor cells showed characteristic features of HSV-1 infection, i.e. intranuclear inclusion bodies and multinuclear giant cell formation (FIG. 5F). No viral antigen staining was seen in the surrounding brains of these mice or in the brains of control untreated mice. This was confirmed by a non-isotopic in situ hybridization protocol using a biotinylated probe for glycoprotein C (gC) and a radiolabeled thymidine kinase (TK) probe (a late and early gene product expressed only in acute infection) to detect active viral replication in serial sections (FIG. 5J). Thus, viral replication, as evidenced by gene expression, is also restricted to the tumor cells. In contrast, tumor-bearing mice inoculated with strain 17+ showed viral replication in both tumor and brain (FIGS. 5K, 5L). Mouse brains harvested 18 days after viral treatment of their tumor implants with 1716 showed a marked decrease in the size of tumor. Indeed only a residual fibrotic scar was seen in some mice, and viral antigen was strictly limited to the remaining cells in the scar (FIG. 5 M, N, O).

To examine the ability of strain 1716 to induce regression of brain tumors, NT2 tumors in the brains of nude mice were stereotactically injected with strain 1716 twelve days after implantation of NT2 cells. Treated mice were inoculated with $5 \times 10^5$ PFU (in 5 μl) of strain 1716 at the tumor implantation site and control mice received 5 μl medium alone. MRI scans showed that these mice developed detectable tumors by 11 days post-implantation. In all mock treated tumor-bearing mice, the tumor grew rapidly in size and was lethan (FIG. 6A-D). In all treated mice, strain 1716 infection induced a detectable regression of the tumor at the original inoculation site (FIG. 6E-G).

To determine whether transplanted NT2N cells were permissive for HSV replication, $2.5 \times 10^5$ cells were transplanted into the brain parenchyma or ventricles of nude mice (Table 1; Study III). These cells integrate and survive for over a year and acquire a fully mature post-natal human CNS neuronal phenotype (27). Strain 1716 was then inoculated at the same stereotactic site 6 weeks post-implantation. The grafts were identified and distinguished from mouse cells by using human specific (MOC1 and RMO301) and mouse specific (RMO93) antibodies to neural cell adhesion molecule (MOC1) or neurofilament proteins (RMO301, RMO93). In contrast to NT2 tumors, these long-term NT2N transplants were non-permissive for strain 1716 replication as evidenced by lack of immunohistochemical staining for viral antigens at days 1,3,5,7,9,21 and 50 post-viral inoculation.

Example 9

HSV Strain 1716 Induces A Non-Apoptotic Death In NT2 Tumor Cells

Sections of tumor from a selected group of strain 1716 infected mice and uninfected tumor controls were prepared for EM analysis to characterise the mode of cell death in the NT2 cell tumors. The infected cells on H&E staining had the characteristics typical of HSV infected cells (FIG. 5F). Viral assembly domains can be seen in the nucleus of infected cells. There was no evidence for an apoptotic mechanism of cell death in the virally infected tumor cells by EM (FIG. 7). Tumor cells with viral particles showed the fragmentation and dissolution of nuclei and organelles as well as condensed and marginated DNA. Terminal deoxynucleotidyl transferase (TdT)dUTP-biotin nick end labeling (TUNEL) and DNA gel electrophoresis studies did not show evidence of DNA fragmentation indicative of apoptosis (data not shown). Taken together, these findings indicate that strain 1716 induces the characteristic lytic infection in the NT2 cells in vitro and in vivo.

Example 10

Long-term Survival of HSV Strain 1716 Treated Tumor-Bearing Mice

Based on the results of the studies described above, we analysed the survival of a cohort of tumor-bearing mice that were or were not treated with virus (Table 2, Studies V and VI). This also enabled us to assess the long-term consequences of treatment with strain 1716 (see below). Twenty mice were inoculated with $3 \times 10^6$ NT2 cells and several days later mice were split into two groups. Control mice received culture medium and treated mice received $5 \times 10^6$ PFU of strain 1716. In the first survival experiment (Table 2, Study V) virus treatment was given at 12 days post-tumor cell inoculation. There was only 1 (10%) long-term survivor in this group and there was no significant difference in survival between control (Study VA) and treated (Study VB) animals (p=0.63, FIG. 8A). Histological examination of some control and treated animals showed that virus was replicating in the tumor. In the treated animals it appears that the tumor had already grown and spread to such a size that one virus treatment was not sufficient to induce regression of the tumor (data not shown). When virus treatment was given at 7 days post-tumor cell inoculation, 44% of the mice survived long-term and 100% of control mice died within 10 weeks (Table 2, Study VI; FIG. 6B). This resulted in a statistically significant improvement in survival (p<0.03; median survival time (controls)=44.75+/−5.24: median survival time (treated)=101.78+/−22.69).

In the survival experiments, significant weight loss was observed in a sub-population of both mock-treated tumor-bearing mice (Table 2, Study VIA) and strain 1716 treated tumor-bearing mice (Table 2, Study VIB). Since there was no difference in the average weights of these two groups (FIG. 8C) we separated the treated group (Study VIB) into two sub-groups (High-Responders (HR)—the long-term survivors (4 mice) and Low-Responders (LR)—mice that died (5 mice); FIG. 8C). We found a significant difference in weight loss at 6 weeks (p<0.01) between groups HR and LR and between groups LR and 1716 treated mice (Study 1) using the standard t-test (FIG. 8D). These data confirmed earlier observations of weight loss in Study V, and they suggest that the weight loss may be due to the toxic physiological effects of tumor growth, regression or lysis and not directly due to an effect of the viral infection of the brain. Notably, some of the treated mice that died showed leakage of tumor cells from implantation site into ventricles and leptomeninges. Since this would lead to obstruction of the flow of cerebrospinal fluid, it is not surprising that some of these treated mice had survival kinetics similar to control mice (FIG. 8A). Finally, intracranial volume of the control mice with brain tumors increased by over 25% (indicating tumor growth) while in treated mice intracranial volume did not increase significantly (see FIG. 6). The long-term survivors also did not have a significant increase in intracranial volume (data not shown). These interpretations are supported by the fact that mice inoculated with strain 1716 alone did not show any clinical or histological characteristics of encephalitis at any time during the study Long-term survivors from studies V and VI (Table 2) had no clinical symptoms, no atypical increase in intracranial volume, and no weight loss (FIG. 8C). These mice and mice inoculated with strain 1716 alone were sacrificed and analysed for pathology and viral replication by immunohistochemistry and in situ hybridisation. In the survivors, there was only evidence of fibrotic scar tissue and dystrophic calcifications but no evidence of residual, live tumor cells (FIG. 9A,B,C). Immunohistochemical staining for cell cycle antigens (e.g. using MIB-1) was also negative suggesting the absence of any cycling NT2 cells in the brain. Further, the brains of these mice were negative for herpes antigens indicating the absence of replicating virus, although in some mice in situ hybridization revealed the presence of latent HSV in the hippocampus (FIG. 9D). Surprisingly, latent virus was also found in the hippocampus of mice infected with strain 1716 along. However, examination of representative rostral to caudal levels of the brains of all survivors using antibodies specific to HSV and to the human NT2 cells (MOC-1, RMO301), did not reveal any evidence of active viral replication nor any residual live tumor cells. To exclude the possible occurrence of other potential toxic sequelae of HSV-1 strains such as demyelination, we probed sections from the brains of mice using antibodies to myelin basic protein. Examination of mice injected with strain 1716 alone as well as long-term survivors revealed no evidence of demyelination (FIG. 9E). Finally, we monitored the levels of poly(A) $^+$RNA by in situ hybridisation using a radiolabeled poly(dT) probe to assess the overall metabolic health of neurons (31,32), and we found no quantifiable difference in the level of poly (A) $^+$RNA between the LAT-positive cells of the long-term survivors versus the contralateral non-LAT positive cells in the same mice and in uninfected, control mice (FIG. 9F).

TABLE 2

Summary of Animal Experiments

| Study | Treatment Tumor | Virus (p.i.[a]) | Number | Survival | Clinical Disease |
|---|---|---|---|---|---|
| I. | — | 1716 | 4 | 100% (>16 wks) | n.a. |
| II. A | — | 17[+] | 10 | n.a.[a] | Encephalitis |
| B | — | 1716 | 10 | n.a. | n.a. |
| C | NT2 | 1716 (12) | 10 | n.a. | n.a. |
| III. | NT2N | 1716 (6 wks) | 10 | n.a. | None |
| IV. A | NT2 | — | 10 | b | None |
| B | NT2 | 1716 (14) | 10 | b | None |
| C | NT2 | 17[+] (14) | 2 | b | Encephalitis |
| V. A | NT2 | — | 10 | 0% (<8 wks) | Cachexia[c] |
| B | NT2 | 1716 (12) | 10 | 10% (>35 wks)[e] | None[d] |
| VI. A | NT2 | — | 8 | 0% (<10 wks) | Cachexia[c] |
| B | NT2 | 1716 (7) | 9 | 44% (>25 wks)[f] | None[d] |

[a]p.i.—post cell implantation when virus or mock inoculum was administered. n.a.—not applicable.
[b]mice were sacrificed at different days after viral inoculation to follow the kinetics of tumor progression and viral spread (see text for details).
[c]These mice also showed no symptoms but the mice that died showed the same range of symptoms as in mock treated mice.
[d]Long-term survivors showed no symptoms but the mice that died showed same range of symptoms as in mock treated mice.
[e]p = 0.63, no statistically significant difference in survival between mock and treated mice.
[f]p < 0.03, statistically significant difference in survival between mock and treated mice.

CONCLUSION

HSV type I (HSV-1) strain 1716 has a deletion in the γ34.5 neurovirulence gene which renders it avirulent in the mouse CNS, we have assessed its potential to induce selective lysis of tumor cells versus neurons in vitro and in vivo. Parental HSV-1 strain 17[+] and engineered strain 1716 were studied using human teratocarcinoma derived embryonal carcinoma cells (NT2 cells). These cells resemble neuronal progenitor cells and can be induced to differentiate into neurons (NT2N) cells) with retinoic acid. Intracerebral grafts of NT2 cells into the brains of nude mice resulted in lethal brain tumors while grafts of NT2N cells resulted in the integration and maturation of NT2N cells without neoplastic reversion. In vitro studies showed that strain 1716 replicates in and spreads on monolayers of NT2 cells, resulting in the lysis of these cells. However, strain 1716 did not replicate in NT2N cells in vitro. In vivo, strain 1716 replicated preferentially in NT2 tumors as evidenced by immunohistochemical staining for viral antigens, in situ hybridisation for HSV specific transcripts and by titration of virus from brains with tumor following intracranial injection of the virus into these mice. In contrast to NT2 tumor cells, transplanted NT2N cells were non-permissive for strain 1716 replication. The temporal regression of NT2 tumors in mice treated with strain 1716 was demonstrated in vivo by Magnetic Resonance Imaging. Electron microscopy and studies of DNA fragmentation suggested that regression of NT2 brain tumors in strain 1716 treated mice was mainly due to a non-apoptotic, lytic mode of cell death. Strain 1716 treated NT2 tumor-bearing mice survived over twice as long as mock-treated tumor bearing mice and these differences in survival (25 vs. 9 wks.) were statistically significant (p<0.03). We conclude from these studies that strain 1716, a replication-competent, non-neurovirulent mutant of HSV-1, induces regression of human neural tumors established in the brains of nude mice resulting in their prolonged survival. These results indicate that HSV-1 γ34.5 mutants are candidates for the treatment of human brain tumors in vivo.

LITERATURE CITED

1. Feun, L. G., et al. The natural history of resectable metastatic melanoma (Stage IVA melanoma)., Cancer, 50: 1656-1663, 1982.
2. Markert, J. M., Coen, D. M., Malick, A., Mineta, T., and Martuza, R. L. Expanded spectrum of viral therapy in the treatment of nervous system tumors, J. Neurosurg, 77: 590-594, 1992.
3. Martuza, R. L., Malick, A., Markert, J. M., Ruffner, K. I., and Coen, D. M. Experimental therapy of human glioma by means of a genetically engineered virus mutant, Science, 252: 854-856, 1991.
4. Ram, Z., Culver, K. W., Walibridge, S., Blaese, R. M., and Oldfield, E. H. In situ retroviral-mediated gene transfer for the treatment of brain tumors in rats, Cancer Res, 53: 83-88, 1993.
5. Takamiya, Y., Short, M. P., Moolten, F. L., Fleet, C., Mineta, R., Breakefield, X. O., and Martuza, R. L. An experimental model of retrovirus gene therapy for malignant brain tumors, J. Neurosurg, 79: 104-110, 1993.
6. Reichard, K. W., Lorence, R. M., Cascino, C. J., Peeples, M. E., Walter, R. J., Fernando, M. B., Reyes, H. M., and Greager, J. A. Newcastle Disease Virus Selectively Kills Human Tumor Cells, J. Surg. Res., 52: 448-453, 1992.
7. Dupressoir, T., Vanacker, J.-M., Cornelis, J. J., Duponchel, N., and Rommelacre, J. Inhibition by parvovirus H-1 of the formation of tumors in nude mice and colonies in vitro by transformed human mammary epithelial cells, Cancer Res, 49: 3203-3208, 1989.
8. Coen, D. M., Kosz-Vnenchak, M., Jacobson, J. G., Leib, D. A., Bogard, C. L., Schaffer, P. A., Tyler, K. L., and Knipe, K. M. Thymidine kinase-negative herpes simplex virus mutants establish latency in mouse trigeminal ganglia but do not reactivate., Proc. Natl. Acad. Sci. USA, 86: 4736-4740., 1989.
9. Tenser, R. B. Role of herpes simplex virus thymidine kinase expression in viral pathogenesis and latency, Intervirology, 32: 76-92, 1991.
10. Coen, D. M., JR., H. E. F. Leslie, L. K., and Retondo, M. J. Sensitivity of arabinosyladenine-resistant mutants of herpes simplex virus to other antiviral drugs and mapping of drug hypersensitivity mutations to the DNA polymerase locus, J. Virol., 53: 477-488, 1985.
11. Ackermann, M., Longnecker, R., Roizman, B., and Pereira, L. Identification, properties, and gene location of a novel glycoprotein specified by herpes simplex virus 1, Virology, 150: 207-220, 1986.
12. Chou, J., Kern, E. R., Whitley, R. J., and Roizman, B. Mapping of herpes simplex virus neurovirulence to gamma 1 34.5, a gene nonessential for growth in culture, Science, 250: 1262-1266, 1990.
13. McGeoch, D. J., Cunningham, C., McIntyre, G., and Dolan, A. Comparative sequence analysis of the long repeat regions and adjoining parts of the long unique regions in the genomes of herpes simplex viruses types 1 and 2, J. Gen. Virol, 69: 1531-1574, 1991.
14. Bolovan, C. A., Sawtell, N. M., and Thompson, R. L. ICP 34.5 mutants of herpes simplex virus type 1 strain 17syn+ are attenuated for neurovirulence in mice and for replication in confluent primary mouse embryo cell cultures, J. Virol, 68: 48, 1994.
15. Javier, R. T., Thompson, R. L., and Stevens, J. G. Genetic and biological analyses of a herpes simplex virus intertypic recombinant reduced specifically for neurovirulence, J. Virol., 61: 1978-1984, 1987.
16. MacLean, A. R., Ul-Fareed, M., Robertson, L., Harland, J., and Brown, S. M. Herpes Simplex virus type 1 deletion variants 1714 and 1716 pinpoint neurovirulence-related sequences in Glasgow strain 17+ between immediate early gene 1 and the 'a' sequence, J. Gen. Virol, 72: 631-639, 1991.
17. Markert, J. M., Malick, A., Coen, D. M., and Martuza, R. L. reduction and elimination of encephalitis in an experimental glioma therapy model with attenuated herpes simplex mutants that retain susceptibility to acyclovir, Neurosurgery, 32: 597-603, 1993.
18. Einhorn, L. H., Burgess, M. A., Vallejos, C., G. P. Bodey, S., Gutterman, J., and Mayligit, G. Prognostic correlations and response to treatment in advanced metastatic malignant melanoma, Cancer Res, 34: 1995-2011, 1974.
19. Amer, M. H., Al-Sarraf, M., Baker, L. H., and Vaitkevicius, V. K. Malignant melanoma and central nervous system metastases: incidence, diagnosis, treatment and survival, Cancer, 42: 660-668, 1978.
20. Budman, D. R., Camacho, E., and Wittes, R. E. The current causes of death in patients with malignant melanoma, Eur. J. Cancer, 14: 327-330, 1978.
21. Patel, J. K., Didolkar, M. S., Pickren, J. W., and Moore, R. H. Metastatic pattern of malignant melanoma. A study of 216 autopsy cases, Am. J. Surg, 135: 807-810, 1978.
22. delaMonte, S. M., Moore, G. W., and Hutchins, G. M. Patterned distribution of metastases from malignant melanoma in humans, Cancer Res, 43: 3427-3433, 1983.
23. Balch, C. M., Soong, S.-j., Murad, T. M., Smith, J. W., Maddox, W. A., and Durant, J. R. A multifactorial analysis of melanoma: IV. Prognostic factors in 200 melanoma patients with distant metastases (stage III), J. Clin. Oncol, 1: 126-132, 1983.
24. Spivack, J. G. and Fraser, N. W. Detection of herpes simplex type 1 transcripts during latent infection in mice, J. Virol., 61: 3841-3847, 1987.
25. McGeoch, D. J. et al. The complete DNA sequence of the long Unique Region in the Genome of Herpes Simplex Virus Type 1, J. Gen. Virol. 69, 1531-1574 (1988).
26. Valyi-Nagy, T, M U Fareed, J S O'Keefe, R M Gesser, A R MacLean, S M Brown, et al., The HSV-1 strain 17+ gamma 34.5 deletion mutant 1716 is avirulent in SCID mice, J, Gen. Virol, 1994; 75; 2059-2063.
27. Kleppner, S R, J Q Trojanowski, and W M-Y Lee, Long-term survival and maturation of neurons derived from the human ell line N-Tera-2 after transplantation into nude mouse. Soc. Neurosci. Abst, 1992; 18:782.
28. Pleasure, S J and V M-Y Lee, NTera 2 cells: A human cell line which displays characteristics expected of a human committed neuronal progenitor cell. J. Neurosci. Res., 1993: 35(6): 585-602.
29. Pleasure, S J, C Page, and V M-Y Lee, Pure post-mitotic, polarised human neurons derived from NTera 2 cells provide a system for expressing exogenous proteins in terminally differentiated neurons. J. Neurosci., 1992; 12(5): 1802-1815.
30. Valyi-Nagy, T, S L Deshmane, B Raengasakulrach, M Nicosia, R M Gesser, M Wysocka, et al., Herpes simplex virus type 1 mutant strain in 1814 establishes a unique, slowly progressing infection in SCID mice. J. Virol., 1992; 66: 7336-7345.
31. Deckwerth, T L and J E. M. Johnson, Temporal analysis of events associated with programmed cell death (apoptosis)

of sympathetic neurons deprived of nerve growth factor. J. Cell Biol., 1993; 123(5): 1207-1222.

32. Freeman, R S, S Estus, and J E. M. Johnson, Analysis of cell cycle-related gene expression in postmitotic neurons: selective induction of Cyclin D1 during programmed cell death, Neuron, 1994; 12(2): 343-355.

33. Deatly, A M, J G Spivack, E Lavi, DR O'Boyle II, and NW Fraser, Latent herpes simplex virus type 1 transcripts in peripheral and central nervour system tissues of mice map to similar regions of the viral genome. J. Virol., 1988; 62: 749-756.

34. Spivack, J G and N W Fraser, Detection of herpes simplex type 1 transcripts during latent infection in mice. J. Viral., 1987; 61:3841-3847.

35. Trojanowski, J, R. Mantione, J Lee, D Seid, T You, L Inge, et al., Neurons Derived from a Human Teratocariconma Cell Line Establishes Molecular and Structural Polarity Following Transplantation into the Roden Brain. Experimental Neurology, 1993; 122: 283-294.

36. Trojanowski, J Q, K-M Fung, L B Rorke, T Tohyama, A T Yachnis, and V-Y Lee, In vivo and in vitro models of medulloblastomas and other primitive neuroectodermal brain tumors of childhood. Mol. Chem. Neuropath, 1994; 21(2-3): 219-239.

37. Fung, KM, DM Chikaraishi, C Suri, F Theuring, A Messing, D M Albert, et al., Molecular phenotype of simian virus 40 large T antigen-induced primitive neuroectodermal tumors in four different lines of transgenic mice. Lab Invest., 1994; 70: 114-124.

38. Adams, R L, D R Springall, M M Levene, and T E Bushell, The immunocytochemical detection of herpes simplex virus in cervical smears—a valuable technique for routine use. J. Pathol, 1984; 143(4): 241-247.

39. Yachnis, A T, L B Rorke, and V M Lee, Expression of neuronal and glial polypeptides during histogenesis of the human cerebellar cortex including observations on the dentate nucleus. J. Comp. Neurol., 1993; 334: 356-369.

40. Wang, J Y and K T Montone, A rapid simple in situ hybridization method for herpes simplex virus employing a synthetic biotin-labeled oligonucleotide probe; a comparison with immunohistochemical methods for HSV detection. J. Clin. Lab Anal., 1994; 8: 105-115.

41. Valy-Nagy, T, S L Deshmane, J G Spivack, I Steiner, C I Ace, C M Preston, et al., Investigation of herpes simplex virus type 1 (HSV-1) gene expression and DNA synthesis during the establishment of latent infection by an HSV-1 variant, in 1814, that does not replicate in mouse trigeminal ganglia. J. Gen. Virol, 1991; 72: 641-649.

42. Huang, S, T J Deernick, M H Ellisman, and D L Spector, In vivo analysis of the stability and transport of nuclear poly(A) +RNA. J. Cell Biol., 1994; 126: 887-899.

43. Baserga, R and D Malamud, Autoradiography: Techniques and Applications. 1969, New York: Harper and Row. p. 129-144.

44. Ferrer, I, T Serrano, and E Soriano, Naturally occurring cell death in the subicular complex and hippocampus in the rat during development. Neurosci. Res., 1990; 8(1): 60-66.

45. Perry, L J and D J McGeoch, The DNA sequences of the long repeat region and adjoining parts of the long unique region in the genome of herpes simplex virus type 1. J. Gen. Virol., 1988; 69: 2831-2846.

The invention claimed is:

1. A method of treating a melanoma in a human, the method comprising the step of administering herpes simplex virus type 1 (HSV-1) to said human, wherein the HSV-1 comprises a mutation in each γ34.5 gene, wherein the HSV-1 is avirulent, and wherein the HSV-1 infects, replicates within, and lyses tumor cells of the melanoma, and wherein the melanoma is a metastasized melanoma.

2. A method according to claim 1 wherein the step of administering the HSV-1 comprises intratumoral injection of the HSV-1.

3. A method according to claim 1 wherein the step of administering the HSV-1 comprises injection of the HSV-1 into the blood stream feeding the melanoma.

4. A method according to claim 1 wherein the HSV-1 is a strain 17 virus.

5. A method according to claim 1 wherein said mutation is within the BamHI s restriction fragment of the $R_L$ terminal repeat corresponding to between 0-0.02 and 0.81-0.83 map units (mu).

6. A method according to claim 1 wherein said mutation comprises a deletion within the BamHI s restriction fragment of the $R_L$ terminal repeat corresponding to between 0-0.02 and 0.81-0.83 map units (mu), wherein the deletion is from 0.1 to 3 kb.

7. A method according to claim 1 wherein said mutation comprises a deletion within the BamHI s restriction fragment of the $R_L$ terminal repeat corresponding to between 0-0.02 and 0.81-0.83 map units (mu), wherein the deletion is from 0.7 to 2.5 kb.

8. A method according to claim 1 wherein said mutation comprises a deletion within the BamHI s restriction fragment of the $R_L$ terminal repeat corresponding to between 0-0.02 and 0.81-0.83 map units (mu), wherein the deletion is a 759 bp deletion in the 34.5 gene.

9. A method according to claim 1 wherein the mutation is a deletion, insertion, or substitution.)

10. A method according to claim 1 wherein the genome of said HSV-1 consists of the genome of a wild type HSV-1 virus having a mutation in each γ34.5 gene.

11. A method according to claim 1 wherein the HSV-1 is HSV1716.

12. The method of claim 1, wherein the HSV-1 is mutated, the mutation consisting of a mutation in each γ34.5 gene.

13. A method of treating a melanoma in a human, the method comprising the step of administering HSV1716 to said human, wherein the HSV1716 is avirulent, and wherein the HSV1716 infects, replicates within, and lyses tumor cells of the melanoma, and wherein the melanoma is a metastasized melanoma.

14. A method according to claim 13 wherein the step of administering the HSV1716 comprises intratumoral injection of HSV1716.

15. A method according to claim 13 wherein the step of administering the HSV1716 comprises injection into the blood stream feeding the tumor.

* * * * *

SEQUENCE LISTING

```
<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
cggggcgggg gtggccgggg g                                             21
```